(12) United States Patent
Fisker

(10) Patent No.: US 10,105,196 B2
(45) Date of Patent: Oct. 23, 2018

(54) MODELING AND MANUFACTURING THE SUPERSTRUCTURE FOR A DENTURE

(75) Inventor: Rune Fisker, Virum (DK)

(73) Assignee: 3SHAPE A/S, Copenhagen K (DK)

( * ) Notice: Subject to any disclaimer, the term of this patent is extended or adjusted under 35 U.S.C. 154(b) by 1344 days.

(21) Appl. No.: 13/996,559

(22) PCT Filed: Dec. 19, 2011

(86) PCT No.: PCT/DK2011/050495
§ 371 (c)(1),
(2), (4) Date: Oct. 10, 2013

(87) PCT Pub. No.: WO2012/083959
PCT Pub. Date: Jun. 28, 2012

(65) Prior Publication Data
US 2014/0051037 A1    Feb. 20, 2014

Related U.S. Application Data

(60) Provisional application No. 61/426,695, filed on Dec. 23, 2010.

(30) Foreign Application Priority Data

Dec. 22, 2010 (DK) ................................ 2010 01175

(51) Int. Cl.
| | | |
|---|---|---|
| *A61C 1/08* | (2006.01) | |
| *A61C 8/00* | (2006.01) | |
| *A61C 13/00* | (2006.01) | |
| *A61C 13/225* | (2006.01) | |
| *A61C 13/34* | (2006.01) | |
| *A61C 13/01* | (2006.01) | |
| *A61C 13/267* | (2006.01) | |

(52) U.S. Cl.
CPC .............. *A61C 8/00* (2013.01); *A61C 8/0048* (2013.01); *A61C 13/0004* (2013.01); *A61C 13/225* (2013.01); *A61C 13/34* (2013.01); *A61C 13/01* (2013.01); *A61C 13/267* (2013.01)

(58) Field of Classification Search
None
See application file for complete search history.

(56) References Cited

U.S. PATENT DOCUMENTS

| | | |
|---|---|---|
| 5,725,376 A | 3/1998 | Poirier |
| 2001/0036617 A1 | 11/2001 | Karmaker et al. |
| 2002/0102517 A1 | 8/2002 | Poirier |
| 2006/0127858 A1 | 6/2006 | Wen |
| 2010/0021859 A1 | 1/2010 | Kopelman |

*Primary Examiner* — Joseph Woitach
(74) *Attorney, Agent, or Firm* — Buchanan Ingersoll & Rooney PC

(57) ABSTRACT

The present invention relates to a system and a method for providing a model of a superstructure joining a denture and a corresponding dental arch, the method comprising the steps of:
obtaining a first 3D representation of at least a part of a preliminary model of the denture,
obtaining a second 3D representation of at least a part of the dental arch comprising dental implants, and
generating a model of a superstructure based on the first 3D representation, the second 3D representation, dental implant positions and dental implant orientations.

31 Claims, 23 Drawing Sheets

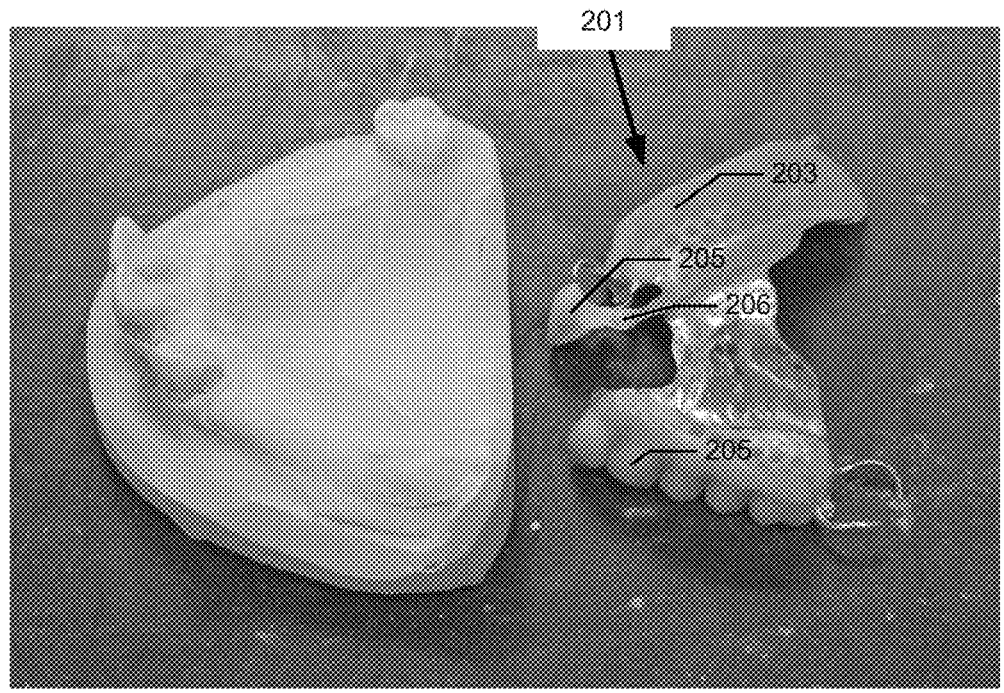
Fig. 2a)
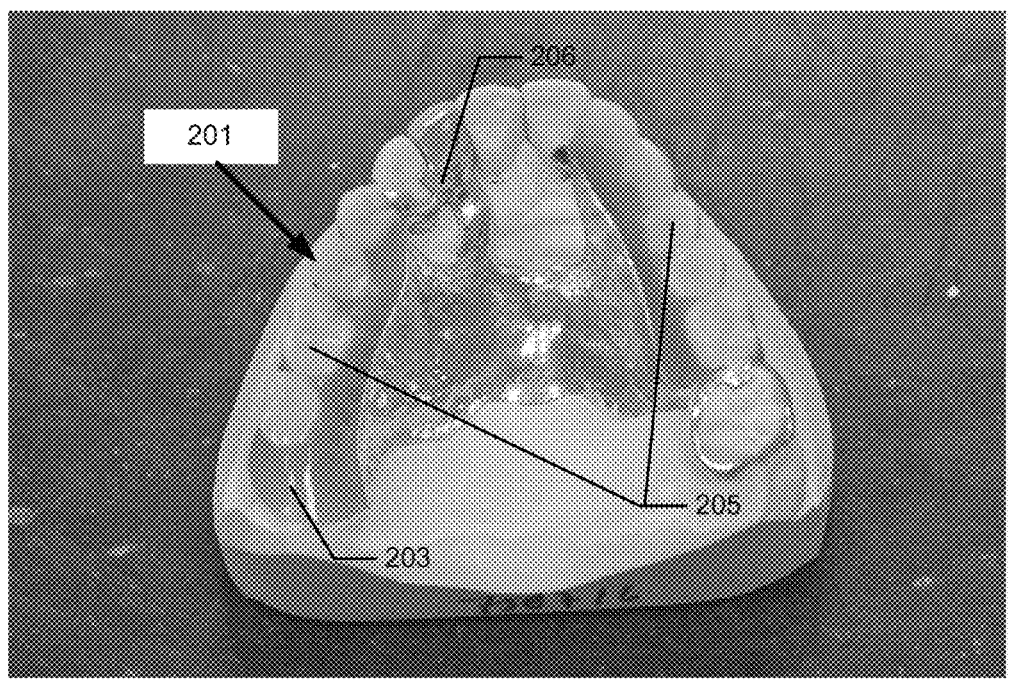

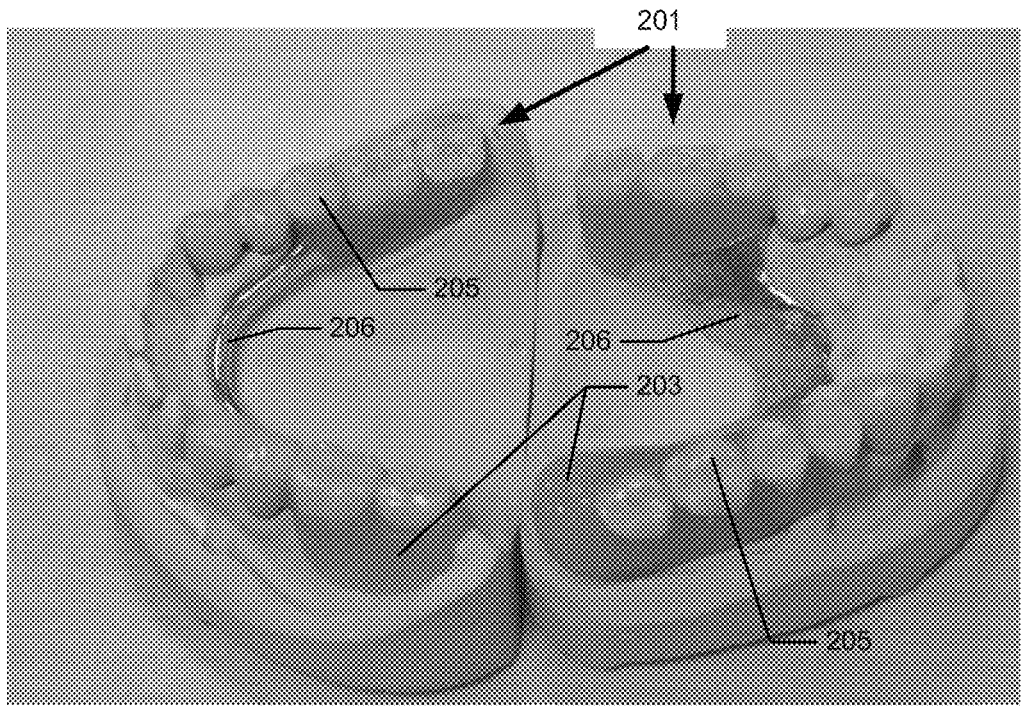
Fig. 2b)
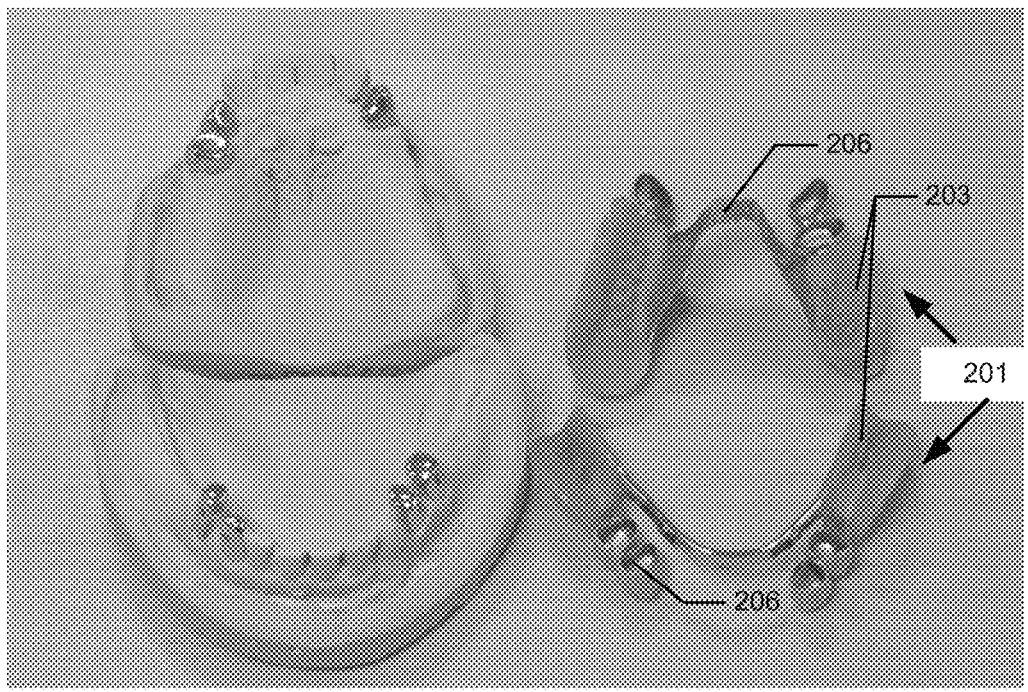

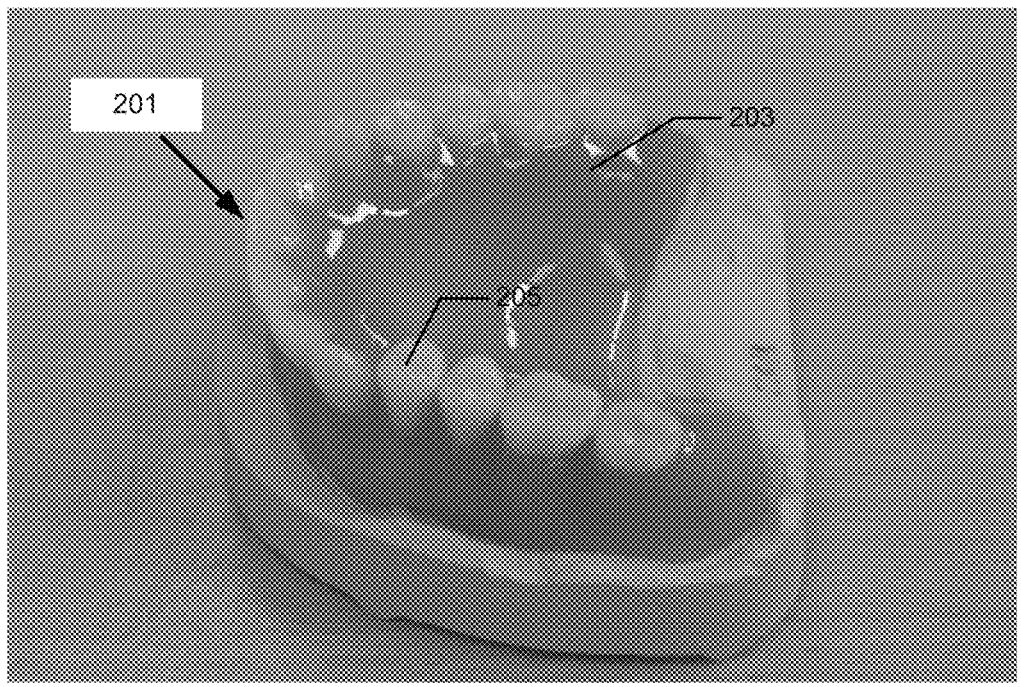
Fig. 2c)
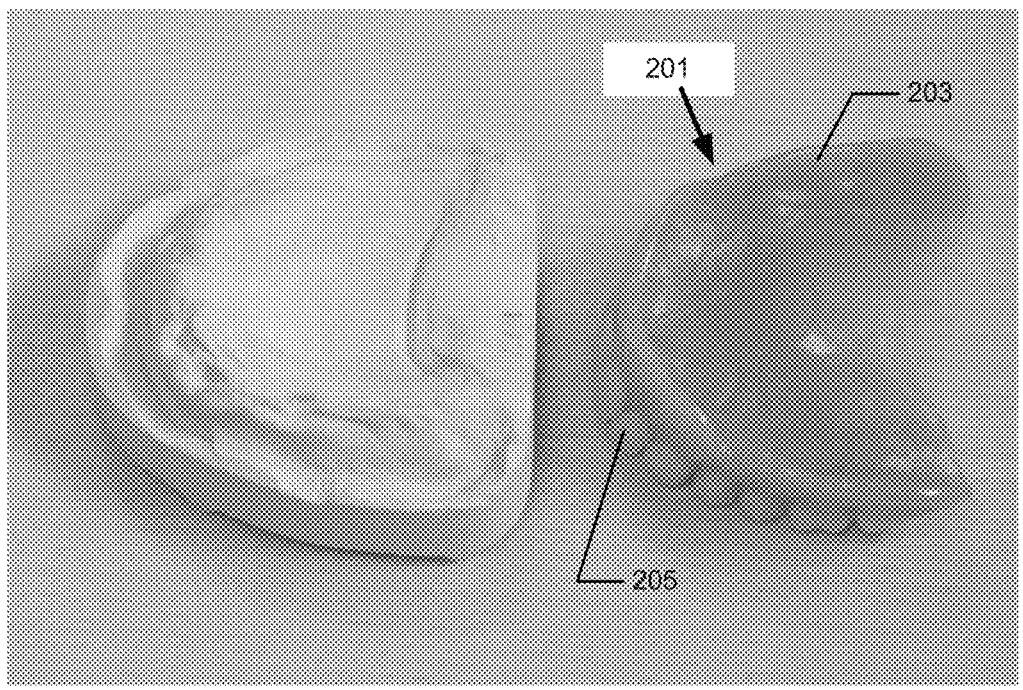

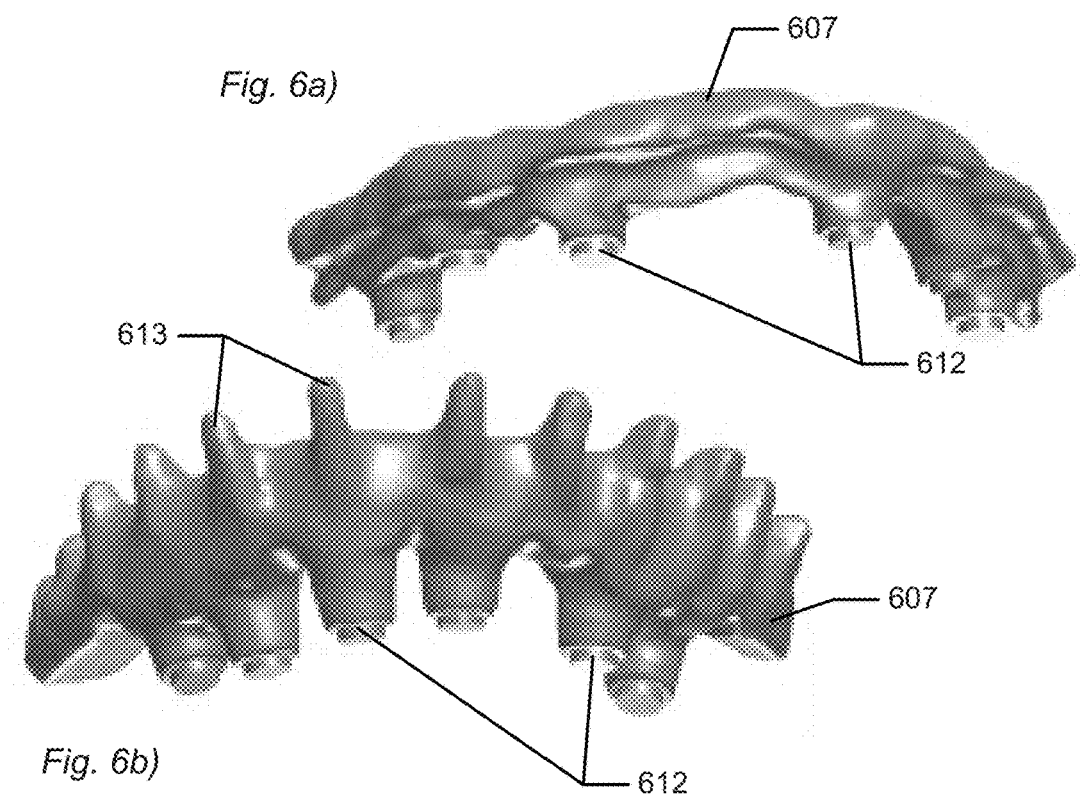
Fig. 6a)
Fig. 6b)
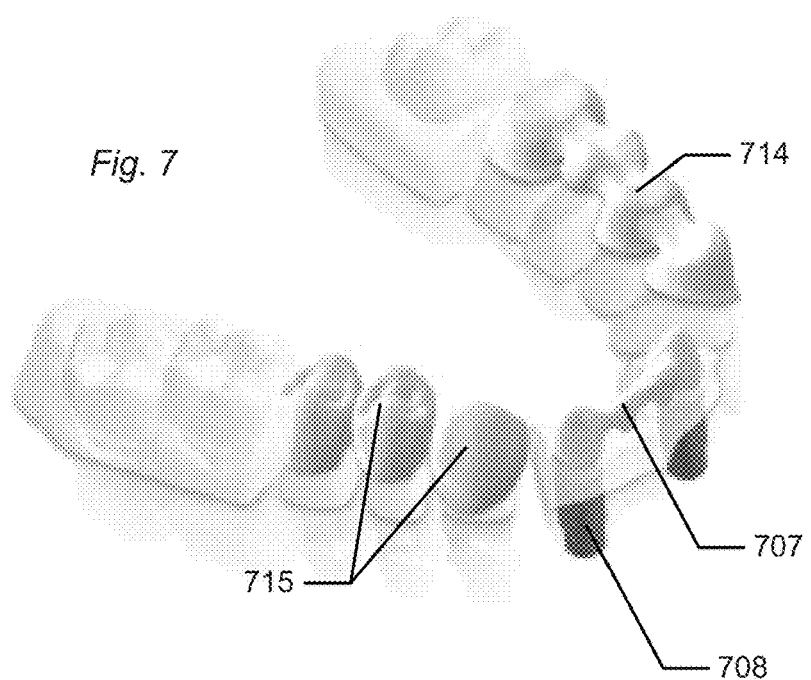
Fig. 7

+

=

I + II  *Fig. 14c)*
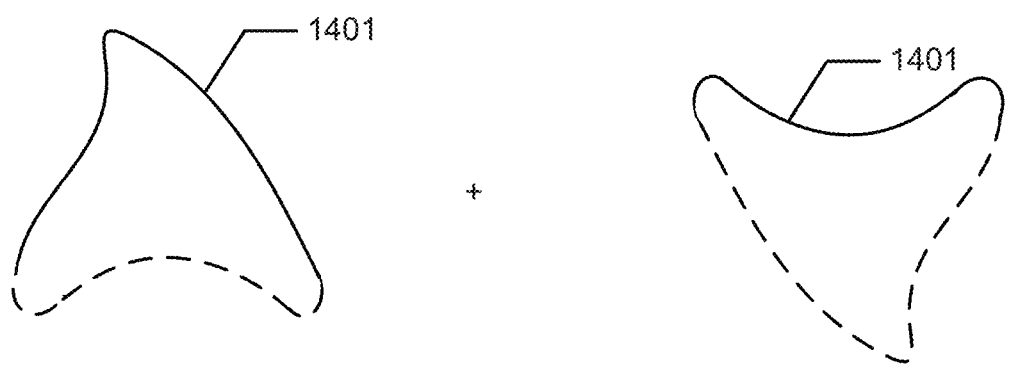
=  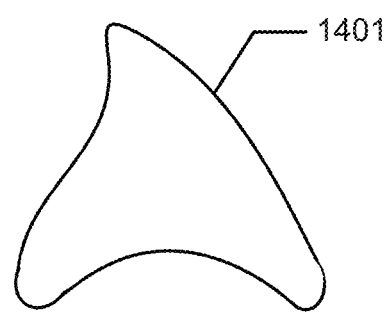  III

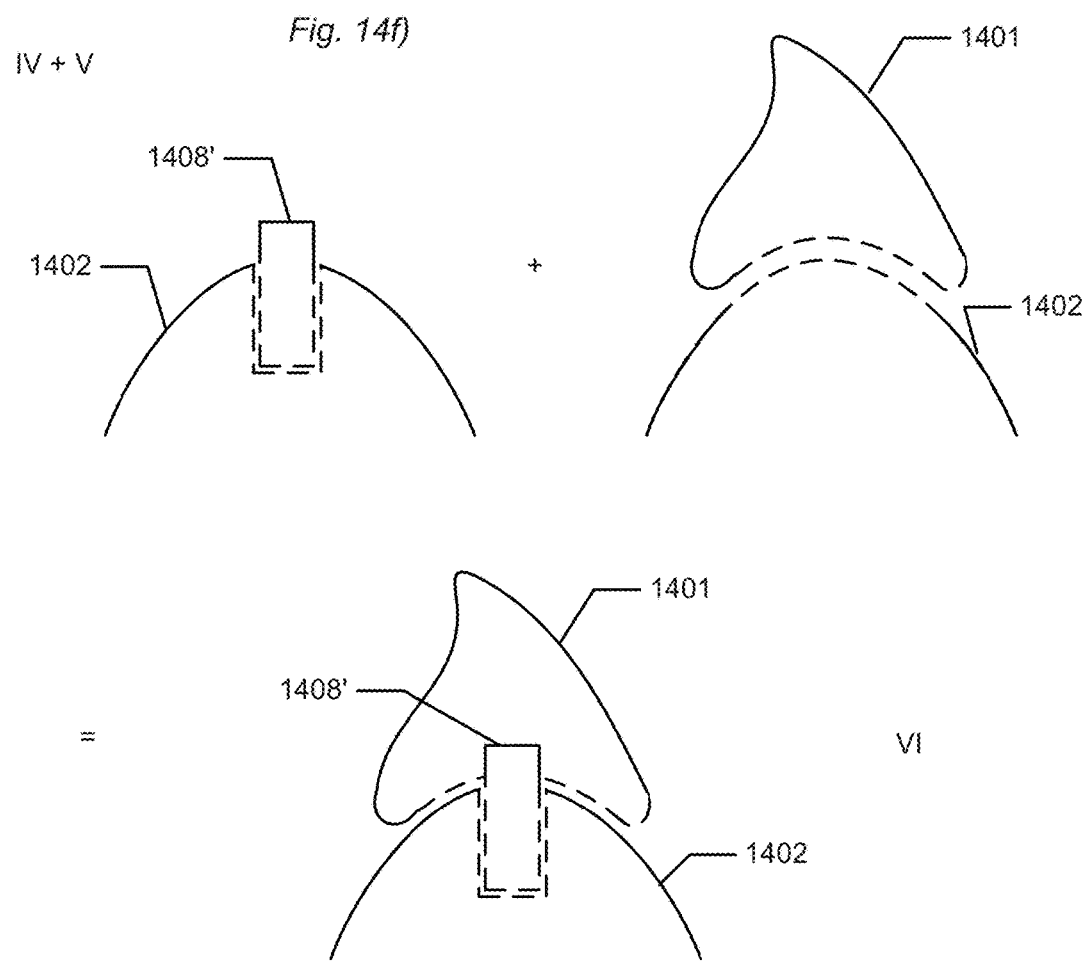

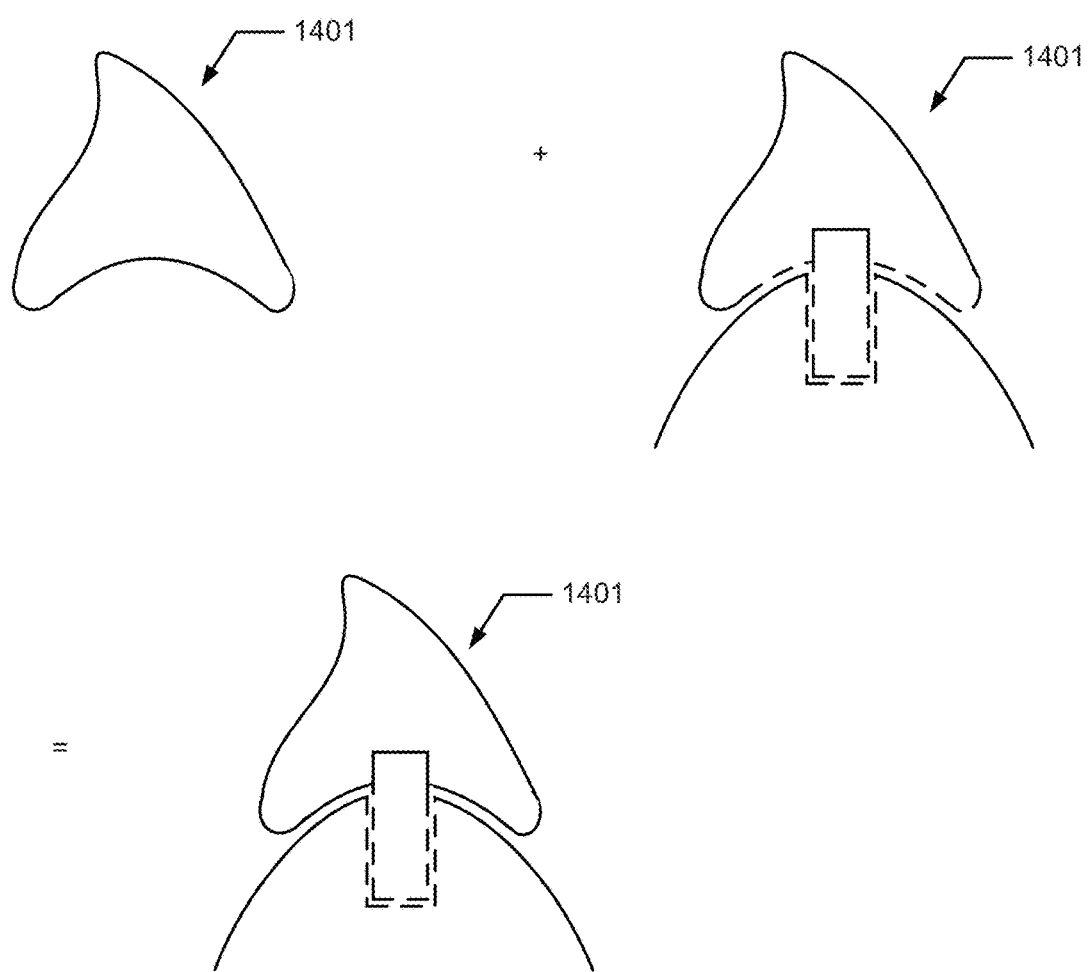

MODELING AND MANUFACTURING THE SUPERSTRUCTURE FOR A DENTURE

The present invention relates to a system and a method for designing and manufacturing a denture and a structure for attachment of the denture.

BACKGROUND OF THE INVENTION

Current processes for manufacturing dentures involve taking an impression of the palate, maxillary and/or the mandibular arch in the oral cavity and manufacturing a wax-up or gypsum model based on the impression. A physical model of the denture is then built on top of the gypsum/wax-up model of the oral cavity. The fit of the physical denture model can thereby subsequently be tested inside the mouth of the patient. If the denture model is manufactured in a flexible material like wax it can be further modified to fit the patient. What remains is the cumbersome process of manually shaping and manufacturing the final denture and the solid base attaching the denture in the mouth of the patient. This solid base must be perfectly fitted to the final denture and the mouth of the patient.

SUMMARY OF THE INVENTION

The prior art process is very cumbersome, may involve several attempts, and generally takes two to six weeks. The resulting denture is neither user friendly nor is it customizable. Also, the resulting denture encounters frequent problems including sore spots, lack of hold and retention, and bacterial growth that may lead to malodor and associated health problems.

Disclosed is a method for providing a model of a superstructure joining a denture and a corresponding dental arch, the method comprising the steps of:
  obtaining a first 3D representation of at least a part of a preliminary model of the denture,
  obtaining a second 3D representation of at least a part of the dental arch comprising dental implants, and
  generating a model of a superstructure based on the first 3D representation, the second 3D representation, dental implant positions and dental implant orientations.

Consequently, it is an advantage that a superstructure for a denture, can be virtually provided and designed based on obtaining a preliminary model of a denture, such as by 3D scanning, and obtaining the patient's dental arch comprising implants of the patient, also such as by 3D scanning. Scanning the dental arch comprising implants or implant analogs will provide the implant positions and orientations in the dental arch.

In some embodiments generating a model of a superstructure is further based on template superstructure elements and/or predefined dental and superstructure parameters.

In some embodiments the method further comprises:
  combining the first and second 3D representations to provide a third 3D representation of at least part of the preliminary model of the denture where the gingival side of the third 3D representation corresponds to the second 3D representation.

In some embodiments the method further comprises virtually modeling a superstructure based on the second 3D representation and/or the third 3D representation.

In some embodiments the method further comprises virtually modeling the final denture based on the third 3D representation, wherein individual teeth and gingiva are segmented and each tooth is provided with an individual cut-back depending on position in the dental arch.

In some embodiments at least a part of the preliminary model of the denture comprises the teeth side.

In some embodiments at least a part of the preliminary model of the denture comprises the gingival side.

In some embodiments providing at least part of the preliminary model of the denture comprises providing the entire preliminary model of the denture.

In some embodiments generating a model of a superstructure is automatic.

One object of the invention is to improve the design and manufacturing process of the attachment of a denture. This can be achieved by a first aspect of the invention relating to a method for providing a model of a superstructure joining a denture and a corresponding dental arch, the method comprising the steps of:
  obtaining a first 3D representation of at least a part of the teeth side of a preliminary model of the denture,
  obtaining a second 3D representation of at least a part of the dental arch comprising dental implants,
  combining the first and second 3D representations to provide a third 3D representation of the entire preliminary model of the denture where the gingival side of the third 3D representation corresponds to the second 3D representation, and
  virtually modeling a superstructure based on the second 3D representation and/or the third 3D representation.

This provides an elegant solution to the cumbersome process of providing the attachment of the denture. The preliminary model of the denture is typically hand crafted by a dentist or a dental technician based on e.g. a gypsum model of the patient's maxillary and mandibular arches. The preliminary model of the denture may be a try-in denture, a diagnostic wax-up, a temporary denture etc. Alternatively, the preliminary denture may be an old denture that the patient has been wearing before. By combining the first and second 3D representations it may be avoided to scan the gingival side of the preliminary model of the denture which may be hard to scan due to occlusion problems in the teeth areas. The gingival side of the preliminary model of the denture is like an impression of the teeth side of the dental arch. The dental arch is provided with dental implants and by obtaining the second 3D representation the dental implant positions and typically also the dental implant orientations are provided. Having 3D representations of the dental arch and the preliminary denture the superstructure can be virtually modeled. This superstructure will be the joining link between the denture and the jaw bone via the dental implants and it is crucial for the final denture. The result of this is that the superstructure can be designed and manufactured precisely, as provided by the CAD/CAM modeling and manufacturing described in the present application.

After the superstructure has been provided the denture can be finalized. This may be provided by manually adapting the preliminary model of the denture to the superstructure or a new denture model may be manually built based on the superstructure and the dental arch.

If the preliminary model of the denture provides a good fit to the patient's gums and implants and/or provides a good fit to the physical model of the patient's mouth, then the preliminary model, such as a try-in denture or a wax-up model, may be used as the final denture.

In a further embodiment of the invention the final denture is virtually modeled based on the virtual model of the superstructure, the second 3D representation and the third 3D representation.

A second aspect of the invention relates to a method for automatically providing a model of a superstructure joining a denture and a corresponding dental arch, the method comprising the steps of:

obtaining a first 3D representation of at least a part of a preliminary model of the denture, obtaining a second 3D representation of at least a part of the dental arch comprising dental implants, and automatically generating a model of a superstructure based on the first 3D representation, the second 3D representation, dental implant positions, dental implant orientations, template superstructure elements and pre-defined dental and superstructure parameters.

With a slightly simpler superstructure, such as a dolder bar, the superstructure model may be generated automatically based on geometric considerations and predetermined parameters once 3D representations of the preliminary model of the denture and the dental arch have been obtained. Needless to say an automatic model generation is an efficient process which is a clear improvement over the presently known methods. In a further embodiment of the invention the first and second 3D representations are combined to provide a third 3D representation of the entire preliminary model of the denture where the gingival side of the third 3D representation corresponds to the second 3D representation. Thus, this third 3D representation may also be basis for the automatic generation of the superstructure model.

Some types of dentures are provided with an outer layer of porcelain, veneering. To make space for the veneering an offset or cutback in relation to the preliminary model of the denture may be provided and/or can be necessary. This is typically a cumbersome manual process which is often hand crafted by a dental technician or a dentist thereby complicating the completion of the final denture. Thus, a further object of the invention is to improve the design and manufacturing process of the final denture. This may be achieved by a third aspect of the invention relating to a method for providing a model of a denture for a corresponding dental arch, the method comprising the steps of:

obtaining a first 3D representation of at least a part of the teeth side of a preliminary model of the denture, obtaining a second 3D representation of at least a part of the dental arch comprising dental implants, combining the first and second 3D representations to provide a third 3D representation of the entire preliminary model of the denture where the gingival side of the third 3D representation corresponds to the second 3D representation, and virtually modeling the final denture based on the third 3D representation, wherein individual teeth and gingiva are segmented and each tooth is provided with an individual offset (cut-back), such as a cut-back depending on the type of the tooth or depending on position in the dental arch.

A procedure for providing the cutback for veneering of a denture is hereby provided. By segmenting the individual teeth and gingiva each tooth and possibly also separate areas of the gingiva can be provided by individually determined cut-back. The amount of cut-back may depend on the type of the teeth, e.g. molar, canine or incisor, and the specific position in the dental arch and predetermined parameters may assist in determining the correct cut-back.

In a further embodiment of the invention the cut-back is provided automatically for one or more or all teeth in the virtual denture model. In a further embodiment of the invention a superstructure is virtually modeled based on the second 3D representation and/or the third 3D representation, said superstructure joining the denture and the corresponding dental arch.

Preferably any method stated herein may be computer-implemented.

A 3D representation, aka a 3D digital representation, can be either point clouds, surface, such as faceted and/or meshed, or volumetric. A 3D model, or 3D digital model, can be generated from a 3D representation. Faceted/meshed representations may be preferred over point clouds, but faceted/meshed representations can be generated from point clouds, for example by triangulation. Volumetric models can be obtained with a scanner applying penetrating radiation, such as CT scanners.

A dental restoration CAD model is a virtual computer model of a restoration. CAD models are created in a software program and can be based on one or more 3D models or one or more 3D representations of the patient's teeth. Thus, whereas a 3D model is typically a digital representation of a physical object, a CAD model is a virtual digital model, however possibly at least partly comprising a digital representation of at least a part of a physical object.

A dental restoration is a classical fixed restoration such as inlays/onlays, veneers, crowns, bridges, implant-retained structures etc, but by analogy also removable restorations such as dentures. A dental restoration requires dental restorative work.

Dentures are prosthetic devices constructed to replace missing teeth. A denture is typically supported by surrounding soft and hard tissues of the oral cavity. Conventional dentures are removable however there are many different denture designs, some which rely on bonding or clasping onto teeth or dental implants. In general the dentures referred to herein are implant retained dentures.

A superstructure is a solid structure joining a denture and the dental implants, where the dental implant is the part, such as a screw, e.g. of titanium, that is integrated within the jaw bone. A superstructure can e.g. be a bar, i.e. implant bar, or an implant bridge. In the case of a bar the denture can be removable attached to the bar or the denture can be fixed to the bar. In the case of an implant bridge the denture is typically fixed to the implant bridge but there are several types of dentures, e.g. dentures with acrylic teeth which are attached to the implant bridge or dentures with veneered teeth, i.e. the outer part of the teeth are porcelain to resemble natural teeth. The present invention may be applied in all the cases of different dentures and different superstructure because generally when designing dentures the starting point is a preliminary model of the denture which typically has been crafted on a gypsum model of the corresponding dental arch.

A patient is the person for whom a denture is designed.

The first and second 3D representations are preferably provided by 3D scanning, such as scanning intra orally, impression scanning, model scanning, cast scanning, CT scanning and/or the like scanning methods. Scanning of the object to obtain the 3D representations, i.e. 3D scanning, can be performed by a number of methods and by means of many commercially available 3D scanner systems. Scanning may for example be provided intra orally, scanning an impression of a set of teeth and/or the antagonist, scanning a model of the teeth, scanning a cast of a set of teeth and/or the antagonist, CT scanning and/or the like scanning methods.

There are several commercial systems available for obtaining 3D representations of teeth, e.g. from 3Shape, Cadent and 3M. Among these are intra-oral scanners, e.g.

3Shape Trios®, and scanners for dental impressions or casts thereof, e.g. 3Shape D640, D700 and D710. Scanners can for example be optical scanners, such as laser, structured light etc. Optical scanners generally obtain a 3D digital model of an object's surface. While this model describes geometry, it does not differentiate between any materials or sub-objects that make up the surface. Potentially, scanners with penetrating radiation such as (cone beam) CT scanners, e.g. Imaging Science International's i-CAT, Kodak/Imtec's Iluma, can be used. They have the advantage of providing volumetric models showing also decay inside the teeth, while disadvantages include concerns about radiation dose or high price of treatment.

In the preferred embodiment of the invention the first 3D representation is based on a physical preliminary model of the denture, such as a wax-up of the preliminary denture or a try-in preliminary denture. Further, the second 3D representation may be based on a physical model of the dental arch, such as a gypsum model of the dental arch or the second 3D representation is directly obtained from the dental arch of the patient, such as obtained by intra oral scanning. The dental arch or the model of the dental arch is preferably provided with the dental implants, or models of the dental implants, and when obtaining the second 3D representation the dental implant will be part of this second 3D representation thereby the accurate position of the dental implants and preferably also the orientation of the dental implants are determined. The dental implants may be more or less "hidden" below the gingival, thus in order to better determine the position and orientation the scan abutments, implant analogs etc. may be provided in one or more of the dental implants.

In the preferred embodiment of the invention the first and second 3D representations are acquired in the same coordinate system. This has the advantage that combining, aligning or registration of the two 3D representations is made easier. This may e.g. be provided by using the same 3D scanner for obtaining both 3D representations and first scanning the dental arch and subsequently, without moving the dental arch, scanning the preliminary model of the denture placed on the dental arch or vice versa. Thus, in a further embodiment of the invention the preliminary model of the denture is 3D scanned while positioned on the dental arch or a physical model of the dental arch.

Combination of the first and second 3D representations may include a step of subtracting the first 3D representation and the second 3D representation, because the upper surface of the dental arch, i.e. the second 3D representation, corresponds to the gingival side of the preliminary model of the denture, i.e. the first 3D representation.

The method according to any of the preceding claims, wherein the steps of virtually modeling the superstructure and the final denture are repeated until the final denture and the superstructure are adapted to each other and the dental arch, reflecting that changes in the virtual model of the superstructure is advantageously adapted to changes in the virtual model of the denture and vice versa.

In a further embodiment of the invention the superstructure is a bar or an implant bridge. The bar may be a dolder or a primary structure or the like. Further, the superstructure may be virtually modeled based on one or more templates of a superstructure or template superstructure elements, possibly a library of template superstructure elements. The superstructure template may comprise the type of superstructure and/or a 2D profile of the superstructure. When building or designing a superstructure for a denture there will typically be various design parameters that must be met in order to provide a good foundation for the denture and at the same time provide a good fit which is comfortable for the patient. Thus, there will typically be certain minimum and maximum requirements and certain limitations for the superstructure which may be combined with geometric, physiological and anatomical constraints, limitations and possibilities. However, feeding a number of these rules and constraints the modeling of a superstructure may be provided more or less automatically by computer implemented virtual modeling, because once the necessary 3D representations have been obtained many of the geometrical constraints for the superstructure are provided, e.g. the curvature of the superstructure may be adapted to the curvature of the dental arch, such as curvature in the horizontal plane. Thus, in a further embodiment of the invention the predefined dental and superstructure parameters may be selected from the group of:

minimum, maximum and preferred vertical distances between gingiva and superstructure,
minimum, maximum and preferred vertical distances between superstructure and dental implants,
minimum, maximum and preferred cross sectional area of superstructure, and dental implants.

In a further embodiment of the invention segmenting teeth and gingiva and/or segmenting the individual teeth in the first, second and/or third 3D representation is provided. Segmentation may at least partly be provided by means of a computer implemented algorithm, such as a shortest-path algorithm applied on a 3D matrix representing curvature of the tooth surface. Segmentation may further at least partly be based on texture information in the 3D representations.

In a further embodiment of the invention subtracting an offset (cut-back) relative to the first and/or third 3D representations during the virtual modeling of the final denture is provided. The offset may be a constant offset relative to the entire 3D representation, relative to the occlusal side or relative to the gingival side. Thus, a first offset may be provided relative to the teeth and a second offset may be provided relative to the gingiva. Further, a varying offset may be provided, the value of said varying offset depending on the position in 3D representation and/or dental arch.

In a further embodiment of the invention individual teeth are provided with individual offsets depending on the location of the teeth in the dental arch and/or depending on the type of teeth. An individual tooth may be provided with a varying offset on the occlusal, gingival, facial, e.g. labial surface of an anterior tooth and buccal surface of a posterior tooth, and lingual sides. For example the cutback or offset on the labial surface or buccal surface of a tooth may be bigger or thicker than the cutback on the lingual surface of the tooth, since the veneering on the labial or buccal surface of the tooth may be thicker than the veneering on the lingual surface, as the lingual surface may be less visible.

Virtual modeling according to the present invention preferably provides CAD models, thus in this case resulting in CAD models of the superstructure and the final denture.

In a further embodiment of the invention manufacturing the superstructure and/or the final denture by means of computer aided manufacturing (CAM) is provided.

In some embodiments the method comprises:
scanning the labial and/or buccal surface of the preliminary denture;
scanning the lingual surface of the preliminary denture;
combining the obtained scan of the labial and/or buccal surface with the obtained scan of the lingual surface.

Hereby the entire surfaces of the preliminary denture may be obtained.

In some embodiments the method comprises:
scanning the preliminary denture from the teeth side;
scanning the preliminary denture from the gingival side;
combining the obtained scan of the teeth side with the obtained scan of the gingival side.

Hereby the entire surfaces of the preliminary denture may be obtained.

In some embodiments the method comprises:
scanning the preliminary denture, where the denture is arranged on the dental arch, whereby the teeth side of the denture is obtained;
scanning the dental arch without the preliminary denture, whereby the dental arch is obtained;
combining the obtained scan of the teeth side of the denture with the obtained scan of the dental arch.

Hereby the entire surfaces of the preliminary denture may be obtained, since obtaining the dental arch may correspond to obtaining the gingival side of the preliminary denture. The dental arch may be the dental arch in the patient's mouth, which is scanned using an intra oral scanner, or it may be a physical impression or a physical model of the patient's dental arch, which is scanned in a desktop scanner.

In some embodiments the method comprises:
scanning the preliminary denture, where the denture is arranged on the dental arch, whereby the teeth side of the denture is obtained;
scanning the dental arch without the preliminary denture, where the dental arch comprises an implant bore, whereby the dental arch and the implant bore for an implant in the dental arch is obtained;
combining the obtained scan of the teeth side of the denture with the obtained scan of the dental arch comprising the implant bore.

Hereby the entire surfaces of the preliminary denture may be obtained, since obtaining the dental arch with an implant bore for an implant may correspond to obtaining the gingival side of the preliminary denture. The dental arch may be the dental arch in the patient's mouth, which is scanned using an intra oral scanner, or it may be a physical impression or a physical model of the patient's dental arch, which is scanned in a desktop scanner.

In some embodiments the method comprises:
scanning the dental arch, where an implant or implant analog is arranged in an implant bore in the dental arch, whereby the dental arch and the implant or implant analog are obtained;
scanning the preliminary denture, where the denture is arranged on the dental arch with the implant or implant analog in the implant bore in the dental arch, whereby the teeth side of the denture is obtained;
combining the obtained scan of the dental arch and the implant or implant analog with the obtained scan of the teeth side of the denture.

Hereby the entire surfaces of the preliminary denture may be obtained together with the implant position and orientation. The dental arch may be the dental arch in the patient's mouth, which is scanned using an intra oral scanner, or it may be a physical impression or a physical model of the patient's dental arch, which is scanned in a desktop scanner.

If the superstructure is an implant bridge, the denture may be fixed to the implant bridge and may be a denture with acrylic teeth which are attached to the implant bridge.

In some embodiments the method further comprises modeling pins on the dental implant bridge and corresponding holes in the denture to fit each other.

The pins may be virtually moved to fit in the virtual teeth of the denture. The pins may be free-form shaped or selected from a library or from default templates. The holes may be generated automatically based on the arrangement of the pins. There may also be a cement space in the hole where the pin does not reach down. Pins may be used in a denture for providing extra strength of the denture and/or of the individual artificial teeth.

In some embodiments the method further comprises obtaining the dental implant pins and automatically generating the corresponding holes in the denture to fit the dental implant pins.

The pins may be modeled, selected from a library of dental implant pin templates, or selected from among a number of default pin templates.

In some embodiments the holes in the denture are manufactured according to the corresponding pins in the bridge.

In some embodiments the method further comprises modeling dental implant pins and holes in the denture based on holes in the pre-manufactured teeth.

The holes may be standard holes in the pre-manufactured teeth, they may be modeled, selected from a library of holes templates, or selected from among a number of default holes templates.

In some embodiments the pins in the bridge are manufactured according to the corresponding holes in the gingival.

An aspect of the invention relates to a method for providing a model of a denture for a corresponding dental arch, the method comprising the steps of:
obtaining a first 3D representation of at least a part of a preliminary model of the denture,
obtaining a second 3D representation of at least a part of the dental arch comprising dental implants, and
generating a model of a denture based on the first 3D representation, the second 3D representation, dental implant positions, dental implant orientations, template superstructure elements and predefined dental and superstructure parameters.

An aspect of the invention relates to a method for providing a model of a superstructure joining a denture and a corresponding dental arch, the method comprising the steps of:
obtaining a first 3D representation of at least a part of a preliminary model of the denture,
obtaining a second 3D representation of at least a part of the dental arch comprising dental implants, and
generating a model of a superstructure based on the first 3D representation, the second 3D representation, dental implant positions, dental implant orientations, template superstructure elements and predefined dental and superstructure parameters.

An aspect of the invention relates to a method for providing a model of a denture for a corresponding dental arch, the method comprising the steps of:
obtaining a first 3D representation of at least a part of a preliminary model of the denture,
obtaining a second 3D representation of at least a part of the dental arch comprising dental implants,
combining the first and second 3D representations to provide a third 3D representation of at least part of the preliminary model of the denture where the gingival side of the third 3D representation corresponds to the second 3D representation, and
virtually modeling the final denture based on the third 3D representation, wherein individual teeth and gingiva are segmented and each tooth is provided with an individual cut-back depending on position in the dental arch.

An aspect of the invention relates to a method for providing a model of a superstructure joining a denture and a corresponding dental arch, the method comprising the steps of:
- obtaining a first 3D representation of at least a part of the teeth side of a preliminary model of the denture,
- obtaining a second 3D representation of at least a part of the dental arch comprising dental implants,
- combining the first and second 3D representations to provide a third 3D representation of at least part of the preliminary model of the denture where the gingival side of the third 3D representation corresponds to the second 3D representation, and
- virtually modeling a superstructure based on the second 3D representation and/or the third 3D representation.

An aspect of the invention relates to a method for automatically providing a model of a superstructure joining a denture and a corresponding dental arch, the method comprising the steps of:
- obtaining a first 3D representation of at least a part of a preliminary model of the denture,
- obtaining a second 3D representation of at least a part of the dental arch comprising dental implants, and
- automatically generating a model of a superstructure based on the first 3D representation, the second 3D representation, dental implant positions, dental implant orientations, template superstructure elements and predefined dental and superstructure parameters.

An aspect of the invention relates to a method for providing a model of a denture for a corresponding dental arch, the method comprising the steps of:
- obtaining a first 3D representation of at least a part of the teeth side of a preliminary model of the denture,
- obtaining a second 3D representation of at least a part of the dental arch comprising dental implants,
- combining the first and second 3D representations to provide a third 3D representation of the preliminary model of the denture where the gingival side of the third 3D representation corresponds to the second 3D representation, and
- virtually modeling the final denture based on the third 3D representation, wherein individual teeth and gingiva are segmented and each tooth is provided with an individual cut-back depending on position in the dental arch.

The present invention relates to different aspects including the methods described above and in the following, and corresponding methods, devices, apparatuses, systems, uses and/or product means, each yielding one or more of the benefits and advantages described in connection with the first mentioned aspect, and each having one or more embodiments corresponding to the embodiments described in connection with the first mentioned aspect and/or disclosed in the appended claims.

The invention further relates to systems comprising the means for carrying out any of the methods listed herein.

In particular, disclosed herein is a system for providing a model of a dental component adapted for placement relative to dental implants in the mouth of a patient, the system comprising:
- means for obtaining a first 3D representation of at least a part of a preliminary model of a denture,
- means for obtaining a second 3D representation of at least a part of the dental arch comprising dental implants.

The means for obtaining the 3D representations may be a 3D scanner and software for creating a 3D model based on the scanning.

In particular, disclosed herein is a system for providing a model of a denture for a corresponding dental arch, the system comprising means for:
- obtaining a first 3D representation of at least a part of a preliminary model of the denture,
- obtaining a second 3D representation of at least a part of the dental arch comprising dental implants, and
- generating a model of a denture based on the first 3D representation, the second 3D representation, dental implant positions, dental implant orientations, template superstructure elements and predefined dental and superstructure parameters.

In particular, disclosed herein is a system for providing a model of a superstructure joining a denture and a corresponding dental arch, the system comprising means for:
- obtaining a first 3D representation of at least a part of a preliminary model of the denture,
- obtaining a second 3D representation of at least a part of the dental arch comprising dental implants, and
- generating a model of a superstructure based on the first 3D representation, the second 3D representation, dental implant positions, dental implant orientations, template superstructure elements and predefined dental and superstructure parameters.

In particular, disclosed herein is a system for providing a model of a denture for a corresponding dental arch, the system comprising means for:
- obtaining a first 3D representation of at least a part of a preliminary model of the denture,
- obtaining a second 3D representation of at least a part of the dental arch comprising dental implants,
- combining the first and second 3D representations to provide a third 3D representation of at least part of the preliminary model of the denture where the gingival side of the third 3D representation corresponds to the second 3D representation, and
- virtually modeling the final denture based on the third 3D representation, wherein individual teeth and gingiva are segmented and each tooth is provided with an individual cut-back depending on position in the dental arch.

In particular, disclosed herein is a system for providing a model of a superstructure joining a denture and a corresponding dental arch, the system comprising means for:
- obtaining a first 3D representation of at least a part of the teeth side of a preliminary model of the denture,
- obtaining a second 3D representation of at least a part of the dental arch comprising dental implants,
- combining the first and second 3D representations to provide a third 3D representation of at least part of the preliminary model of the denture where the gingival side of the third 3D representation corresponds to the second 3D representation, and
- virtually modeling a superstructure based on the second 3D representation and/or the third 3D representation.

In particular, disclosed herein is a system for automatically providing a model of a superstructure joining a denture and a corresponding dental arch, the system comprising means for:
- obtaining a first 3D representation of at least a part of a preliminary model of the denture,
- obtaining a second 3D representation of at least a part of the dental arch comprising dental implants, and
- automatically generating a model of a superstructure based on the first 3D representation, the second 3D representation, dental implant positions, dental implant orientations, template superstructure elements and predefined dental and superstructure parameters.

In particular, disclosed herein is a system for providing a model of a denture for a corresponding dental arch, the system comprising means for:
  obtaining a first 3D representation of at least a part of the teeth side of a preliminary model of the denture,
  obtaining a second 3D representation of at least a part of the dental arch comprising dental implants,
  combining the first and second 3D representations to provide a third 3D representation of the preliminary model of the denture where the gingival side of the third 3D representation corresponds to the second 3D representation, and
  virtually modeling the final denture based on the third 3D representation,
wherein individual teeth and gingiva are segmented and each tooth is provided with an individual cut-back depending on position in the dental arch.

In particular, disclosed herein is a system for providing a model of a superstructure joining a denture and a corresponding dental arch, the system comprising:
  means for obtaining a first 3D representation of at least a part of the teeth side of a preliminary model of the denture,
  means for obtaining a second 3D representation of at least a part of the dental arch comprising dental implants,
  means for combining the first and second 3D representations to provide a third 3D representation of the entire preliminary model of the denture where the gingival side of the third 3D representation corresponds to the second 3D representation, and
  means for virtually modeling a superstructure based on the second 3D representation and/or the third 3D representation.

In particular, disclosed herein is a system for automatically providing a model of a superstructure joining a denture and a corresponding dental arch, the system comprising:
  means for obtaining a first 3D representation of at least a part of a preliminary model of the denture,
  means for obtaining a second 3D representation of at least a part of the dental arch comprising dental implants, and
  means for automatically generating a model of a superstructure based on the first 3D representation, the second 3D representation, dental implant positions, dental implant orientations, template superstructure elements and predefined dental and superstructure parameters.

In particular, disclosed herein is a system for providing a model of a denture for a corresponding dental arch, the system comprising:
  obtaining a first 3D representation of at least a part of the teeth side of a preliminary model of the denture,
  obtaining a second 3D representation of at least a part of the dental arch comprising dental implants,
  combining the first and second 3D representations to provide a third 3D representation of the entire preliminary model of the denture where the gingival side of the third 3D representation corresponds to the second 3D representation, and
  virtually modeling the final denture based on the third 3D representation, wherein individual teeth and gingiva are segmented and each tooth is provided with an individual cut-back depending on position in the dental arch.

A further embodiment of the invention relates to a computer program product having a computer readable medium, said computer program product comprising the means for carrying out any of the steps of any of the methods listed herein.

A further embodiment of the invention relates to a computer program product comprising program code means for causing a data processing system to perform any of the herein listed methods when said program code means are executed on the data processing system.

Furthermore, the invention relates to a computer program product comprising program code means for causing a data processing system to perform the any one or more of the methods above, when said program code means are executed on the data processing system, and a computer program product, comprising a computer-readable medium having stored there on the program code means.

DESCRIPTION OF DRAWINGS

The above and/or additional objects, features and advantages of the present invention, will be further elucidated by the following illustrative and non-limiting detailed description of embodiments of the present invention, with reference to the appended drawings, wherein:

FIG. 2 shows examples of manufactured dentures.

FIG. 6 shows examples of implant bridges.

FIG. 7 shows an example of combination of different CAD modeling for a set of teeth.

DETAILED DESCRIPTION OF THE DRAWINGS

In the following description, reference is made to the accompanying figures, which show by way of illustration how the invention may be practiced.

Figure 1:
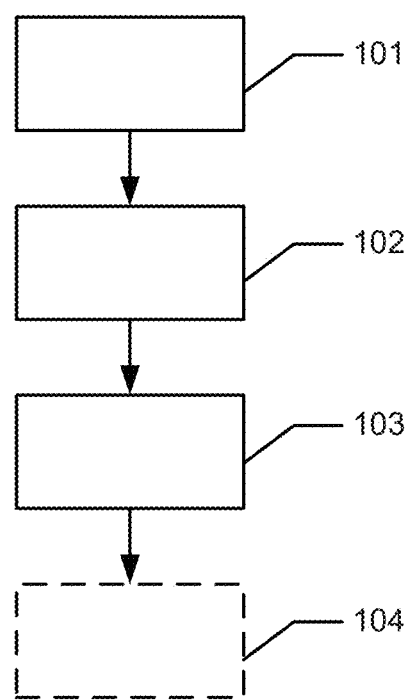
FIG. 1 shows an example of a flowchart illustrating methods for providing a denture.

FIG. 1 shows an example of a flowchart illustrating methods of providing a denture.

The flowchart illustrates a method for providing a model of a superstructure joining a denture and a corresponding dental arch, where in step 101 a first 3D representation of at least a part of the teeth side of a preliminary model of the denture is obtained.

In step 102 a second 3D representation of at least a part of the dental arch comprising dental implants is obtained.

In step 103 the first and second 3D representations are combined to provide a third 3D representation of the entire preliminary model of the denture where the gingival side of the third 3D representation corresponds to the second 3D representation.

In step 104 a superstructure based on the second 3D representation and the third 3D representation is virtually modeled.

The flowchart also illustrates a method for automatically providing a model of a superstructure joining a denture and a corresponding dental arch, where in step 101 a first 3D representation of at least a part of a preliminary model of the denture is obtained.

In step 102 a second 3D representation of at least a part of the dental arch comprising dental implants is obtained.

In step 103 a model of a superstructure based on the first 3D representation, the second 3D representation, dental implant positions, dental implant orientations, template superstructure elements and predefined dental and superstructure parameters is automatically generated.

The flowchart also illustrates a method for providing a model of a denture for a corresponding dental arch, where in step 101 a first 3D representation of at least a part of the teeth side of a preliminary model of the denture is obtained.

In step 102 a second 3D representation of at least a part of the dental arch comprising dental implants is obtained.

In step 103 the first and second 3D representations are combined to provide a third 3D representation of the entire preliminary model of the denture where the gingival side of the third 3D representation corresponds to the second 3D representation.

In step 104 the final denture is virtually modeled based on the third 3D representation, wherein individual teeth and gingiva are segmented and each tooth is provided with an individual cut-back depending on position in the dental arch.

The flowchart also illustrates a method for providing a model of a superstructure joining a denture and a corresponding dental arch.

In step 101 a first 3D representation of at least a part of a preliminary model of the denture is obtained.

In step 102 a second 3D representation of at least a part of the dental arch comprising dental implants is obtained.

In step 103 a model of a superstructure based on the first 3D representation, the second 3D representation, dental implant positions and dental implant orientations is generated.

FIG. 2a shows pictures of a denture 201 which is, or is a part of, or comprises a partial denture. The partial denture 201 comprises a framework 206 and a gingival part 203 and a teeth part comprising artificial acrylic teeth 205. In the top image the partial denture is arranged next to a gypsum model of the patient's present teeth. The denture is seen from below, i.e. from the side pointing towards the palate. This side of a denture is referred to herein as "the gingival side" of the denture. In the bottom image, the partial denture is arranged on the gypsum model of the patient's teeth. The denture is seen from above, i.e. from the side pointing towards the surroundings when the denture is arranged in the mouth of the patient. This side of a denture is referred to herein as "the teeth side" of the denture or "the occlusal side" of the denture.

FIG. 2b) shows pictures of an upper denture and a lower denture 201, which are both partial dentures. The partial dentures 201 comprise a framework 206 and a gingival part 203 and the top image also shows a teeth part comprising artificial acrylic teeth 205. In the top image, the partial dentures are arranged on gypsum models of the patient's present teeth and the dentures are seen from above, i.e. the teeth side. In the bottom image, the partial dentures are arranged next to the models of the patient's teeth and the dentures are seen from below, i.e. the gingival side. In the bottom image the dentures are shown without the artificial teeth or the veneering of the metal framework.

FIG. 2c) shows pictures of a denture 201 which is a full maxillary denture, i.e. a denture for the upper arch. The denture 201 comprises a gingival part 203 and a teeth part comprising artificial teeth 205 made of acrylics. In the top image, the partial denture is arranged on the model of the patient's present teeth and the denture is seen from the teeth side. In the bottom image, the partial denture is arranged next to the model of the patient's teeth and the denture 201 is seen from the gingival side.

The denture 201 shown in FIG. 2c) is a removable denture and it is not attached to the mouth by any attachment means when in use. The patient can therefore at any time remove the denture. The denture 201 of FIG. 2c) is held in place in the patient's mouth by means of friction, suction, negative pressure etc. The dentures 201 of FIG. 2a) and FIG. 2b) may be removable for the patient, however alternatively the dentures may be attached to the existing teeth by some attachment means, which only the dentist should manage.

InteraDent Zahntechnik GmbH in Lübeck, Germany has provided the images of the different dentures shown in FIG. 2.

Figure 3A:
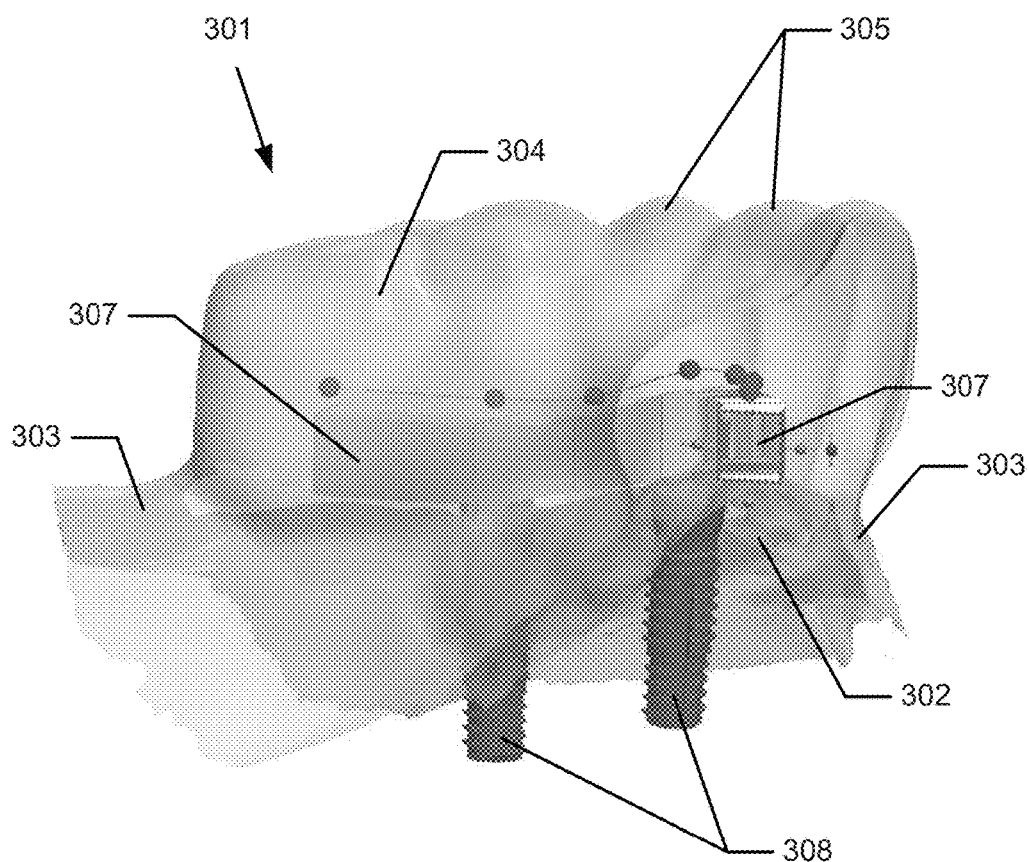
FIG. 3 shows examples of virtual modeling of a denture.

FIG. 3a) shows an example of virtual modeling of a superstructure, such as a bar; an example of a superstructure joining a denture to the dental arch via dental implants anchored in the bone. The virtual denture 301 comprises a virtual teeth part 304 comprising virtual teeth 305, and a virtual gingival part 303. Inside the virtual denture 301, which is shown as transparent, a virtual superstructure, which is an implant bar 307, is seen and marked with dots above it. A number of virtual implant screws 308 are also seen sticking out underneath the denture 301. The implant screws 308 are attached to the implant bar 307 and are supposed to anchor the bar to the bone. A part of a scan 302 of the patient's jaw is also seen inside the denture 301. The bar 307 is modeled for optimal fit to the denture 301 and implants 308 using virtual tools in computer aided drawing (CAD) software. Virtual measurements can be performed to validate space and distances of the denture 301, the scan 302, the bar 307, the implants screws 308 etc. The connection from the bar 307 to the implants 308 can be shaped as a cylindrical extension, as a freeform emergence profile etc.

Figure 3B:
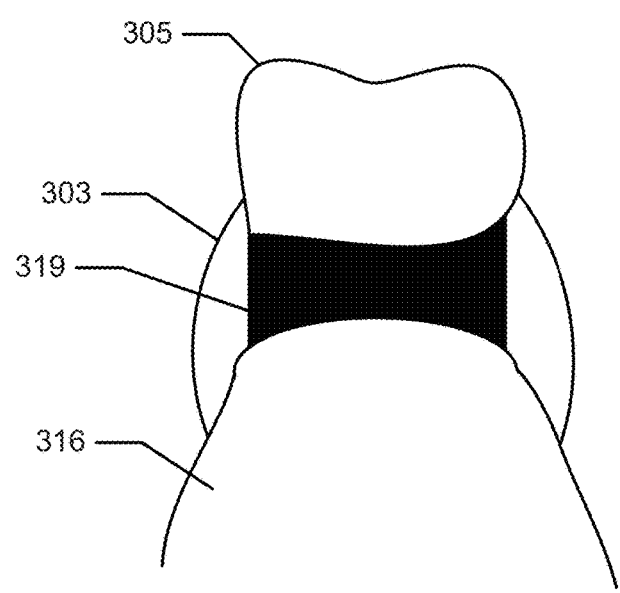

FIG. 3b) shows an exemplary illustration of a virtual modeling of a removable denture. A virtually modeled tooth 305 in a partial removable framework is arranged with a distance to the existing gingival 316, and the space 319 between the tooth and the existing gingival is virtually blocked out for avoiding having the denture material between the teeth and the existing gingival when the manufactured denture is worn by the patient. The gingival part 303 is modeled such that the tooth 305 is attached in the gingival part 303.

Figure 4A:
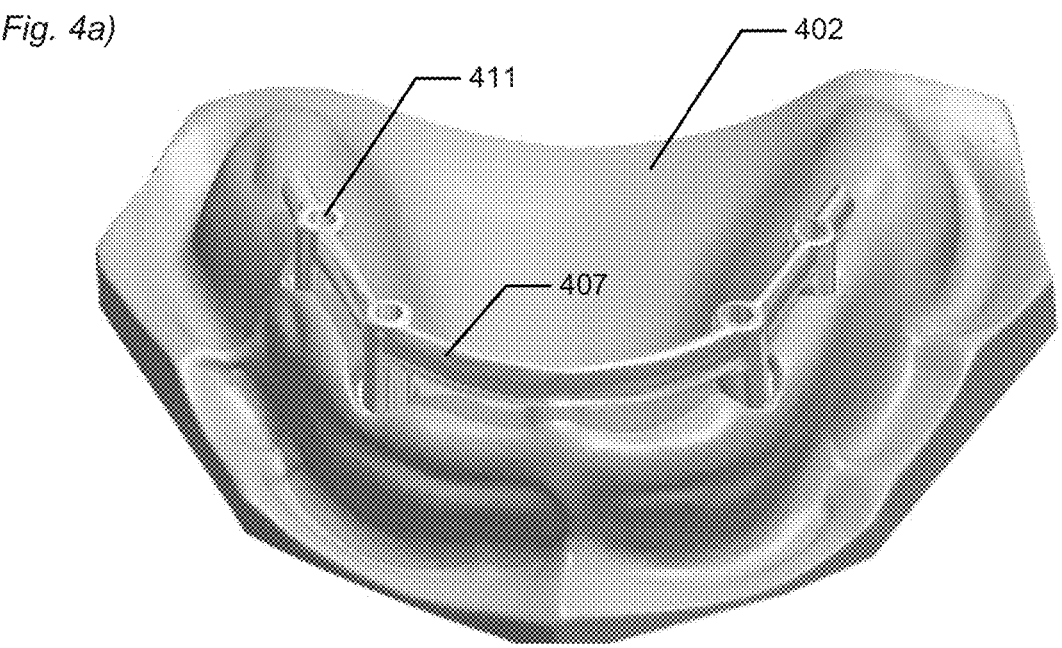
FIG. 4 shows examples of different implant bars.

FIG. 4a) shows an example of superstructure in the form of an implant bar 407 for a full denture (not shown). This type of bar is termed a "dolder". The denture may be a removable denture, i.e. it may be removably attached to the implant bar 407 by means of attachments in the form of e.g. clips (not shown) which can be snapped on and off the implant bar 407. The bar 407 comprises holes 411 for receiving implants. This bar has been automatically generated based on a preliminary model of a denture (not shown). As seen from the figure the bar resembles a fence and the individual elements of the bare may be standard predetermined geometrical forms, such as tubes, cylinders, pipes, etc. The superstructure shown in FIG. 4a) is based on the positions and orientations of the four dental implants (not visible). As seen from the figure the vertical axes of the dental implants are not parallel because the underlying bone structure determines the best orientation of the single implant. Thus, the automatic modeling of the superstructure may be based on starting out with placing the vertical oriented hollow tubes directly on top of the dental implants based on the position and orientation of the dental implants which is known from the second 3D representation of the dental arch. Next the horizontally arranged bars, possibly hollow or solid tubes, are provided to connect the vertical tubes where the curvature of the bars may at least partly follow the curvature of the dental arch. The vertical position where the bars are attached to the vertical tubes can, as previously indicated, be determined from certain predefined constraints in relation to the gingiva. The cross sectional area of the horizontal bar and the vertical tubes may e.g. be determined from certain physical, physiological or anatomical constraints. Attachment clips may also be added automatically to the bar. Thus, general and specific basic rules and requirements may be implemented in the software and thereby automate the provision of a superstructure. Thus, by means of the present invention a superstructure for a denture may be provided by automatic operation implemented in software.

Figure 4B:
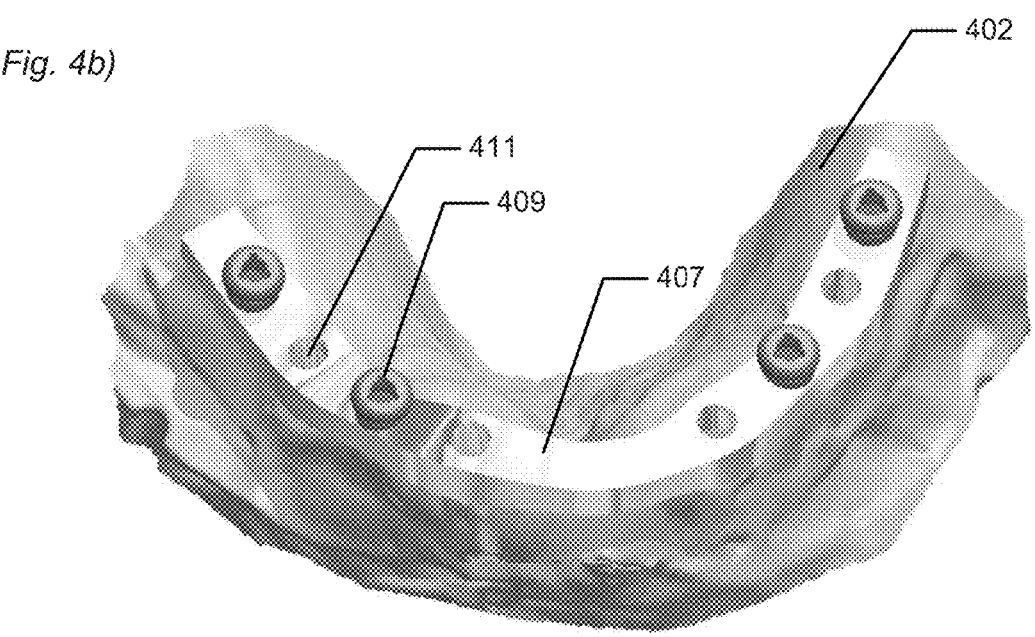

FIG. 4b) shows an example of a superstructure in the form of an implant bar 407 for a full denture (not shown). This type of bar is termed a "primary structure" and may be slightly more complicated to produce. However, it may still be provided automatically by means of the present invention. The denture for this implant bar may be a removable denture, i.e. it may be removably attached to the implant bar 407 by means of attachments 409 in the form of locaters present on both the denture and on the implant bar 407, where the locators 409 enables that the denture can be clicked on and off the implant bar 407. The implant bar 407 comprises holes 411 for receiving implants. The implant bar in FIG. 4b) is still based on standard geometrical forms that follows the curvature of the dental arch; however in this case the thickness and the width of the bar 407 vary along the dental arch. Minimum thickness and width are necessary to provide the necessary strength, but e.g. around the attachment holes the bar 407 is slightly wider and there may further be thinner portion to account for protruding sections of gingiva.

Figure 4C:
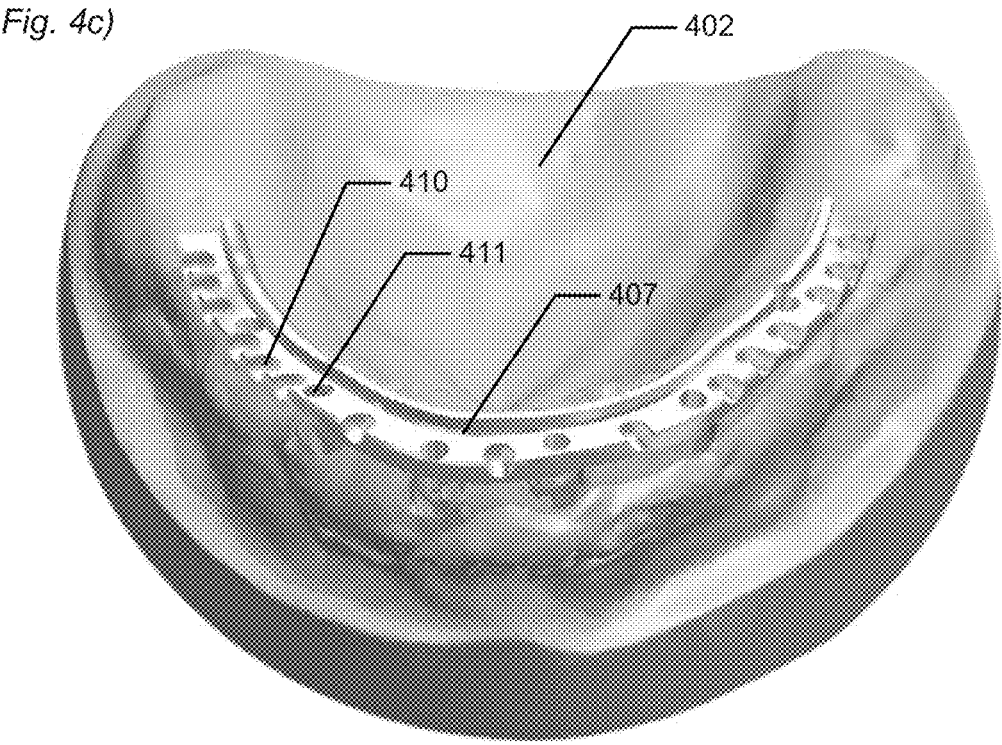

FIG. 4c) shows an example of a superstructure in the form of an implant bar 407 for a full denture (not shown). The denture may be a fixed denture, i.e. it may be fixedly attached to the implant bar 407 e.g. by gluing part of the denture into the retention holes 410 in the implant bar 407. This may be performed by using acrylics in the denture, and the soft acrylics from the denture will then run into the retention holes 410 of the implant bar 407 and thereby attaching the denture to the implant bar 407. The implant bar 407 comprises holes 411 for receiving implants. The implant bar 407 in FIG. 4c) is also modeled automatically.

Figure 5A:
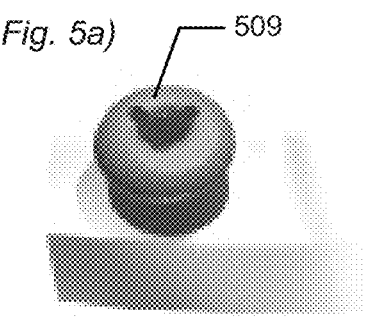
FIG. 5 shows examples of different attachment types.
Figure 5B:
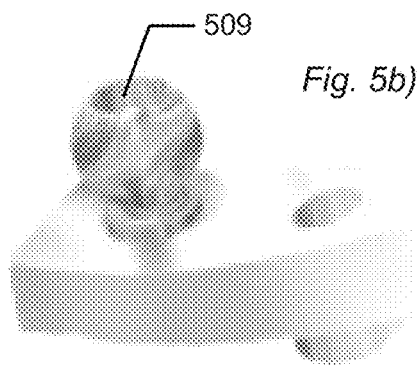
Figure 5C:
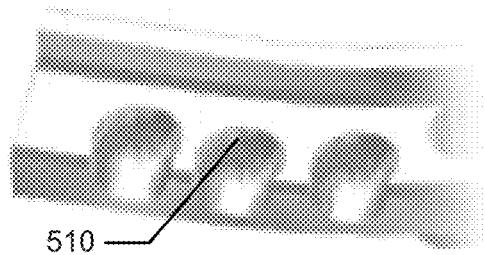

FIG. 5a) shows an attachment in the form of a locator 509. The locator 509 may comprise a male part on e.g. the superstructure in the form of an implant bar and a female part on e.g. the denture or vice versa, and the male part and the female part may work as a button. FIG. 5b) shows an attachment in the form of a ball attachment 509. FIG. 5c) shows an attachment in the form of retention holes 510. Another type of attachment may be a slide attachment; however any kind of attachment from a CAD library may be used. When modeling the denture and implant, the different kinds of attachments can be added anywhere on the implant bar and the attachments can then be rotated and translated for fine-adjustment of their position and angles.

FIG. 6a) shows an example of a superstructure in the form of an implant bridge 607 onto which a full denture is adapted to be arranged. On the side opposite to where the denture should be attached, the implant bridge 607 comprises protrusions 612 from holes for receiving implants (not shown). The implant bridge shown in FIG. 6a) is difficult to model automatically because the final shape of such an implant bridge is customized to the dental arch and the denture and as seen from the figure the implant bridges are not primarily based on standard geometrical forms. However, by means of the present method, it is possible to model such an implant bridge.

FIG. 6b) shows an example of a superstructure in the form of an implant bridge 607 comprising pins 613 where each pin is adapted to receive an artificial tooth having a hole in it for fitting over the pin, or where the pin is adapted to be covered by veneering in the form of e.g. ceramics or composite material for resembling teeth. On the side opposite to the pins 613, the implant bridge 607 comprises protrusions 612 from holes for receiving implants (not shown). The implant bridges shown in FIG. 6b) is difficult to model automatically because the final shape of such an implant bridge is customized to the dental arch and the denture and as seen from the figures the implant bridges are not primarily based on standard geometrical forms. The implant bridge in FIG. 6b) is therefore typically provided by cut-back of the preliminary model of the denture, which may be accomplished by the present invention. From the figure as can be seen that the cut-back vary from tooth to tooth depending on the position of the tooth. The cut-back also varies depending on the type of the tooth and from which side of the tooth the cut-back is provided.

FIG. 7 shows a standard bridge 714, full anatomical crowns 715, a superstructure in the form of an implant bridge 707 and implants 708. A denture can be modeled using CAD and after manufacturing be attached to the implant bridge 707 and e.g. on the standard bridge 714. Alternatively, veneering can be applied to the standard bridge to make it an anatomical bridge, e.g. veneering in the form of porcelain.

Figure 8A:
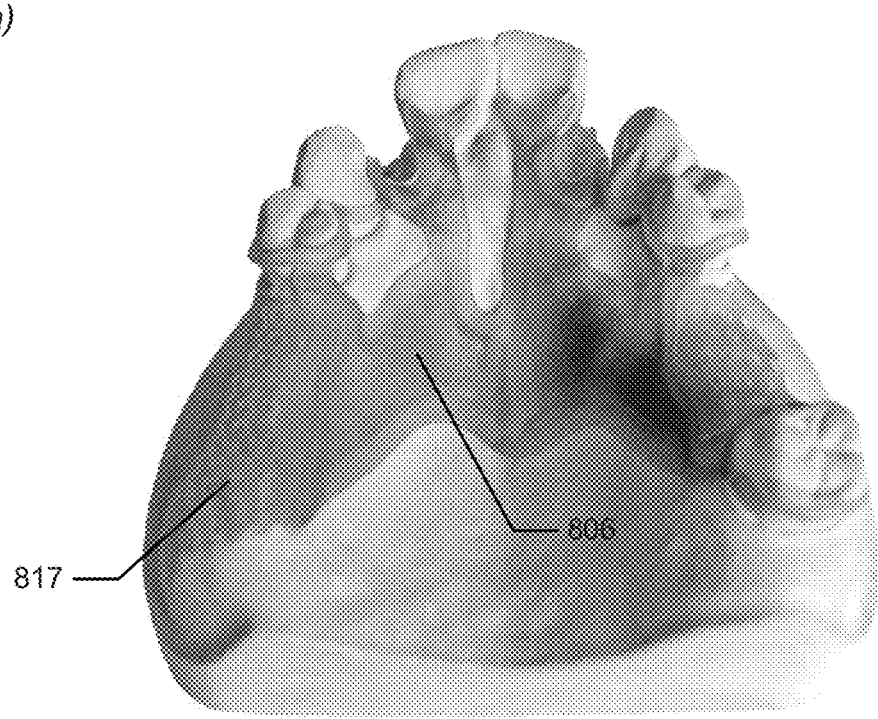
FIG. 8 shows an example of a how a denture and a partial removable framework are attached to each other.
Figure 8B:
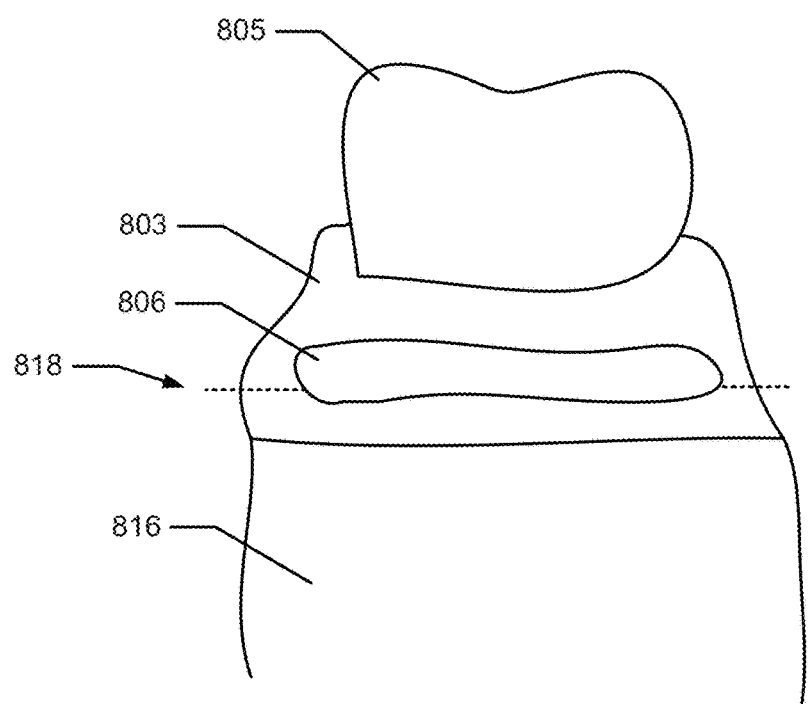

FIG. 8a) shows a partial removable framework 806 with retention grid and holes 817 but without artificial teeth or gingival attached. FIG. 8b) shows a cross section of a denture with a partial removable framework, for example as those seen in FIGS. 2a) and 2b). The partial removable framework 806 is embedded in the gingival part 803, since the gingival part 803 is both present above and below the framework 806. An artificial tooth 805 is arranged in the gingival part and the gingival part 803 rests on the patient's real physiological gingival 816.

If the gingival part 803 is poured in silicone, then the liquid silicone can flow into the holes of the retention grid 817 in the framework 806. But if the gingival part 803 is printed, then there may be no liquid silicone to flow into the holes of the retention grid 817. For the framework 806 and the gingival part 803 to be attached to each other, the gingival part 803 may then be separated as indicated by the separation line 818 into two or more pieces which can then be assembled around the framework 806. The separation line(s) 818 can be at other places in the gingival part 803, e.g. vertical instead of horizontal etc. Alternatively and/or additionally, the framework 806 including the retention grid 817 can be separated into two or more pieces.

FIG. 9 shows examples of modeling the gingival part.

Figure 9A:
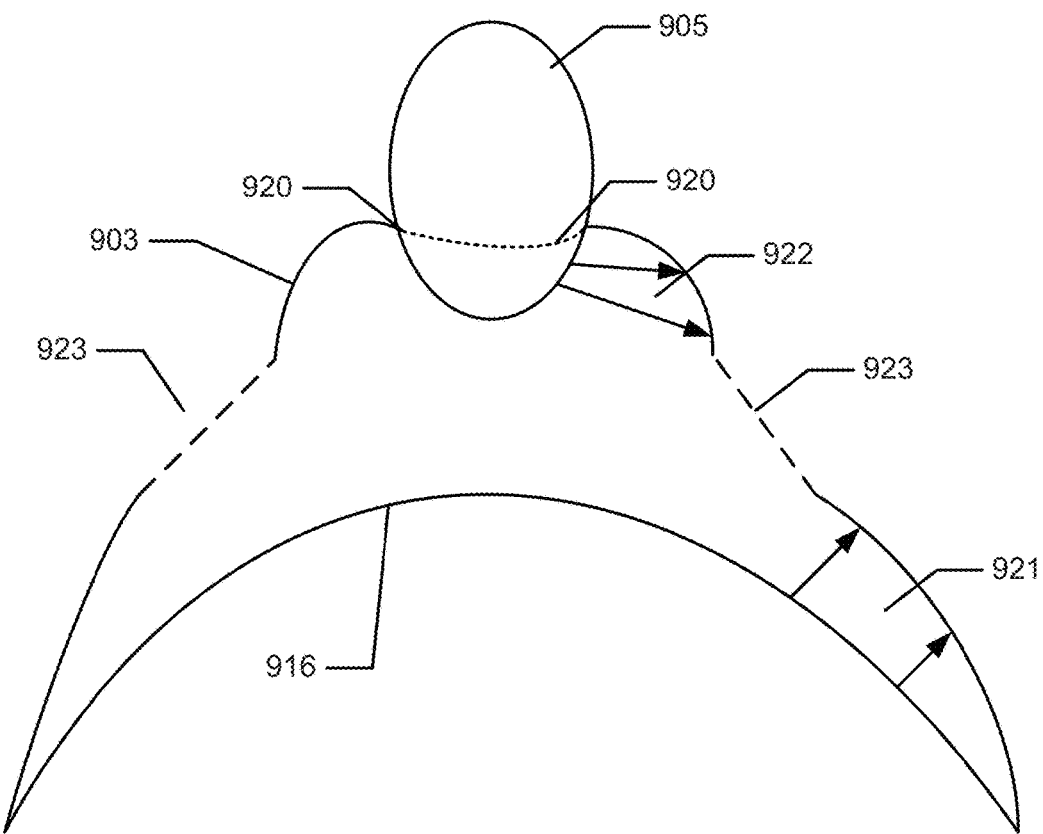
FIG. 9 shows examples of modeling the gingival part.

FIG. 9a) shows points 920 marked on the teeth 905 for indicating that the gingival part 903 should end there. A first offset or cutback 921, marked by arrows, of the gingival part 903 from the existing gingival 916 may be determined, an second offset or cutback, marked by arrows, 922 of the gingival part 903 from the teeth 905 may be determined, a smooth transition 923 connecting the first offset 921 from the existing gingival 916 and the second offset 922 from the teeth may be performed using a lofting operation.

Figure 9B:
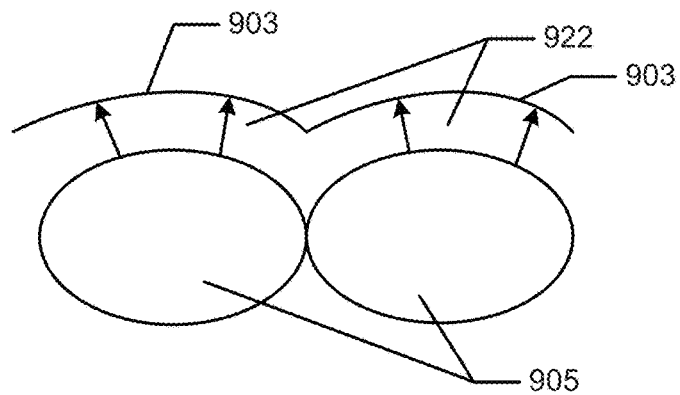

FIG. 9b) shows an example of offsetting 922, marked by arrows, the gingival part 903 around the virtual teeth 905. By offsetting cutting back the gingival part 903 around the virtual teeth 903 and finally around the manufactured teeth, the gingival part 903 will look more natural since this is how the physiological gingival looks.

FIG. 10 shows an example of combining a scanned denture and scanned implant positions in a patient's jaw.

Figure 10A:
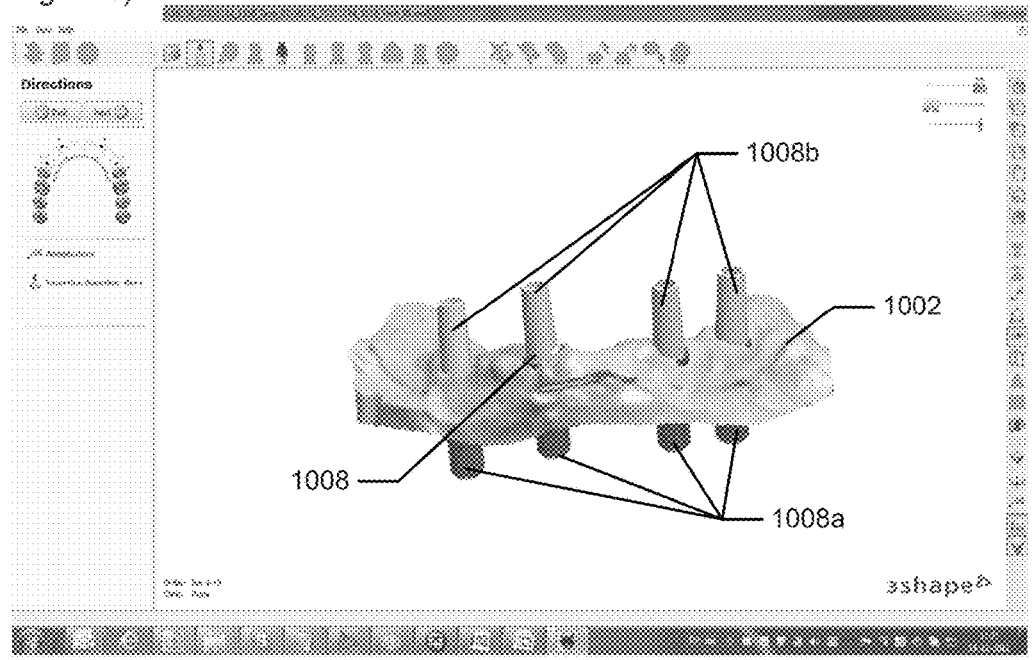
FIG. 10 shows an example of combining a scanned denture and scanned implant positions in a patient's jaw.

FIG. 10a) shows an example of a scan of implants screws 1008 in a patient's jaw 1002. The scan can be performed directly in the patient's mouth using an intra oral scanner, the scan can be performed on a physical impression, and/or the scan can be performed on a physical plaster model of the patient's mouth, where the physical plaster can be obtained by means of a dentist taking a physical impression of the patient's teeth using impression material, and then a dental technician may pour the physical plaster model from the negative impression of the teeth.

The implant screws 1008 may be attached in the jaw bone of the patient and/or attached to an implant superstructure, such as a bar, and the implant screws 1008 may be configured for anchoring the superstructure to the bone. Four implant screws 1008 are shown.

Generally, the implant screws 1008 may be anchored in the jaw bone of the patient before scanning the jaw 1002, the implants may be imitated by means of implant analogs or implant abutments in a physical model of the patient's teeth, and/or the implant screws may be virtually designed to the jaw scan 1002 of the patient, before designing the denture and/or the superstructure.

An implant screw 1008 may comprises the actual bone screw 1008a in the bone and an abutment 1008b, which is configured for attachment to a superstructure and/or for attachment of virtual teeth.

Figure 10B:
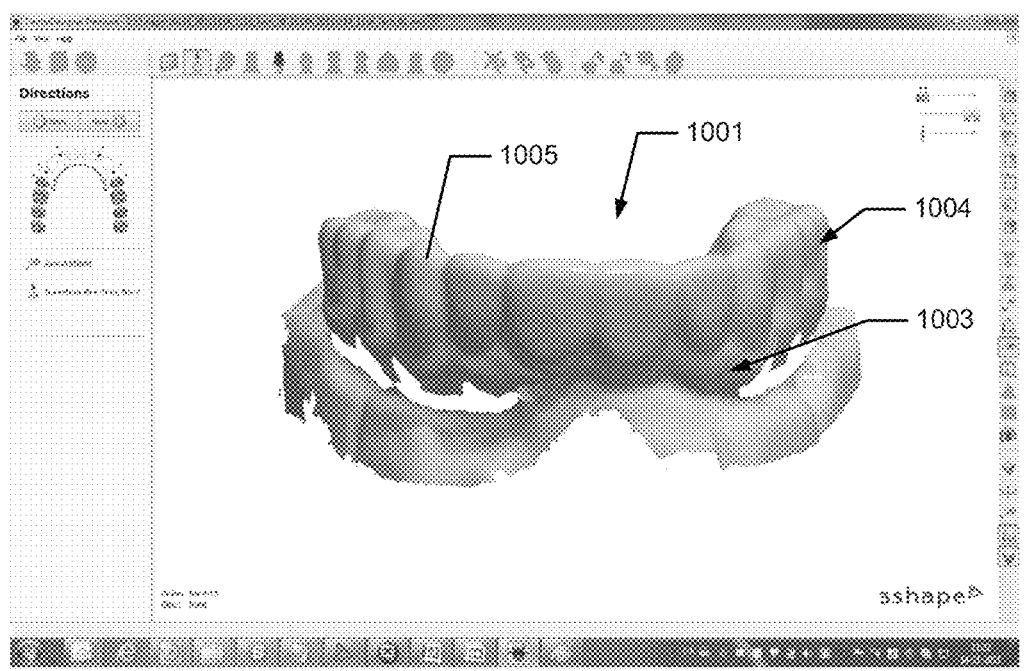

FIG. 10b) shows an example of a virtual denture 1001 comprising a virtual teeth part 1004 comprising virtual teeth 1005, and a virtual gingival part 1003.

Figure 10C:
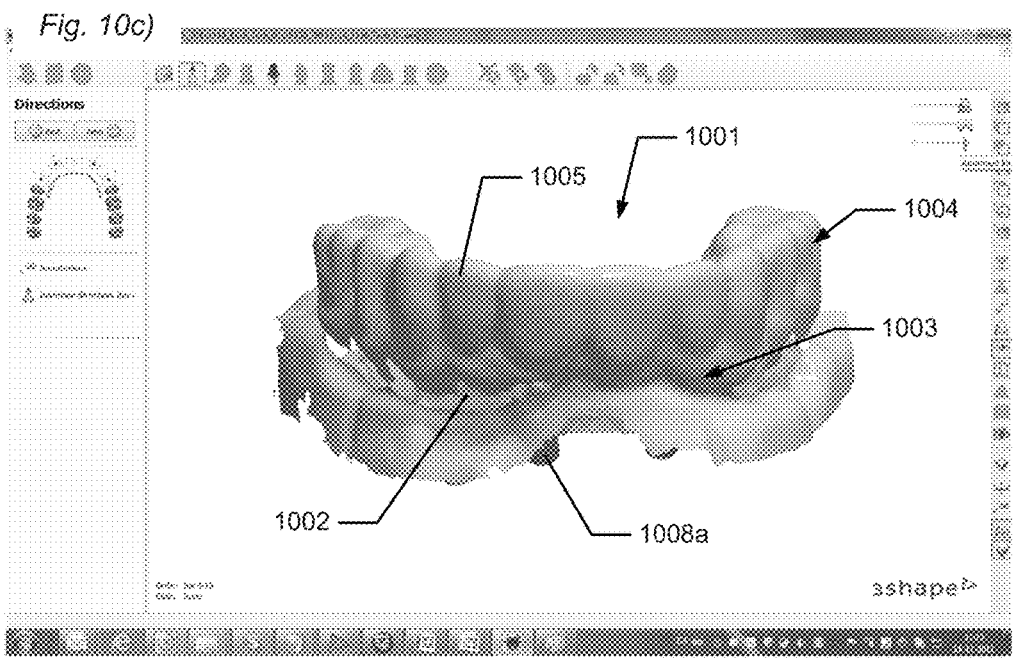

FIG. 10c) shows an example where the virtual denture 1001 from FIG. 10b) is combined with the scan of implant screws in the patient's jaw 1002 from FIG. 10a). The virtual denture 1001 comprises a virtual teeth part 1004 comprising virtual teeth 1005, and a virtual gingival part 1003. From the scan of implant screws one of the screws 1008a can be seen, the rest is hidden behind the denture 1001.

Figure 10D:
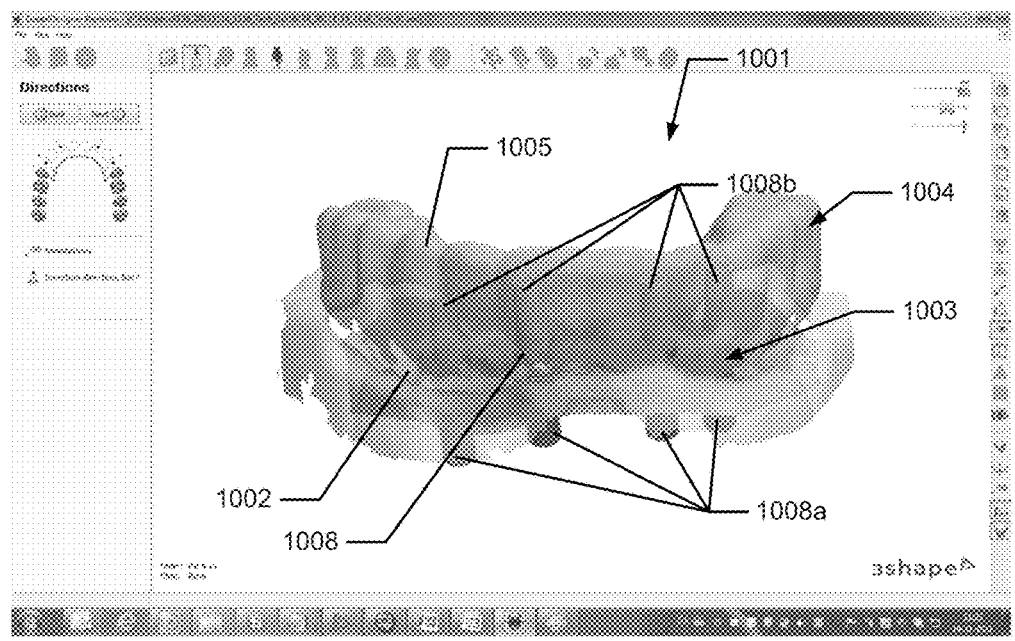

FIG. 10d) shows an example where the virtual denture 1001 is shown as transparent, and the virtual implant screws 1008 are seen sticking out both inside and underneath the denture 1001. The implant screws 1008 may be attached in the jaw bone of the patient and/or attached to an implant superstructure, such as a bar, and the implant screws 1008 are configured for anchoring the superstructure to the bone.

The virtual denture 1001 comprises a virtual teeth part 1004 comprising virtual teeth 1005, and a virtual gingival part 1003.

The implant screws 1008 comprises the actual bone screw 1008a in the bone and an abutment 1008b, which is configured for attachment to a superstructure and/or for attachment of virtual teeth.

FIG. 11 shows examples of a superstructure joining a denture and a corresponding dental arch.

Figure 11A:
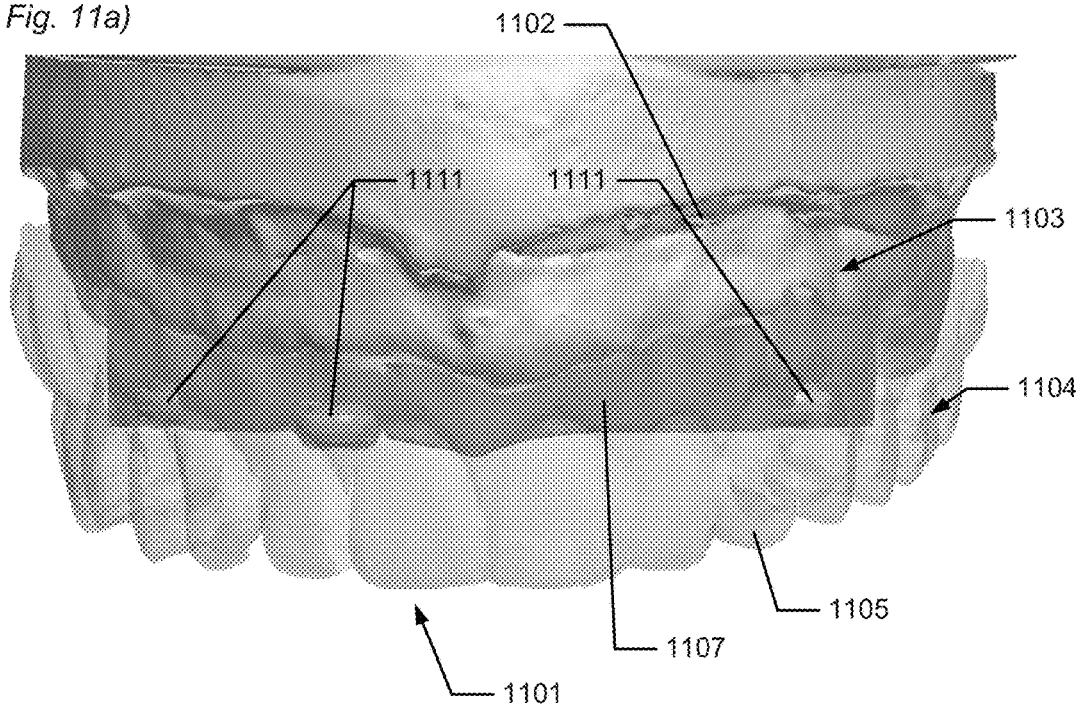
FIG. 11 shows examples of a superstructure joining a denture and a corresponding dental arch.

FIG. 11a) shows an example where the virtual denture 1101 is arranged relative to the scan of the patient's arch 1102 as in FIGS. 10c) and 10d), and where furthermore a superstructure 1107 for joining the denture 1101 and the dental arch 1103 is virtually placed.

The superstructure 1107 comprises holes 1111 for receiving implants. The superstructure may be automatically generated based on a preliminary model of a denture 1101. The denture 1101 shown in FIG. 11a) may be the preliminary model of the denture. However, the denture 1101 shown in FIG. 11a) may alternatively be the final denture.

The superstructure 1107 is modeled for optimal fit to the denture 1101 and implants using virtual tools in computer aided drawing (CAD) software. Virtual measurements can be performed to validate space and distances of the denture 1101, the scan of the dental arch 1102, the superstructure 1107, the holes 1111 etc. The connection from the superstructure 1107 to the implants through the holes 1111 can be shaped as a cylindrical extension, as a freeform emergence profile etc.

Figure 11B:
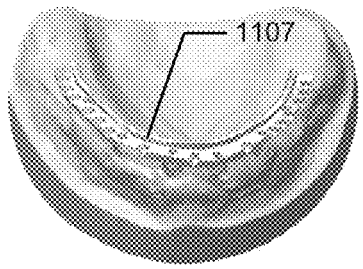
Figure 11C:
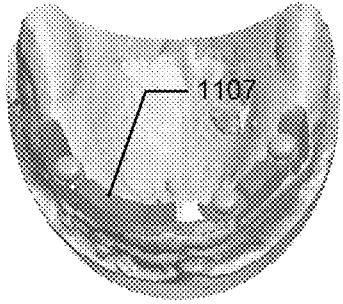
Figure 11D:
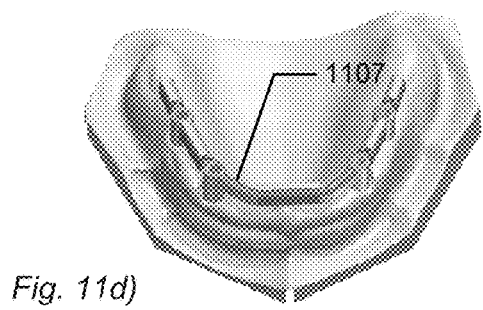
Figure 11E:
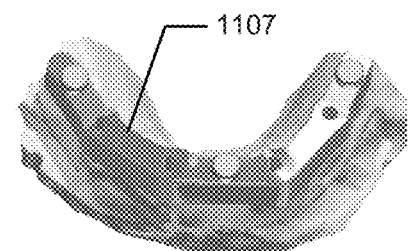
Figure 11F:
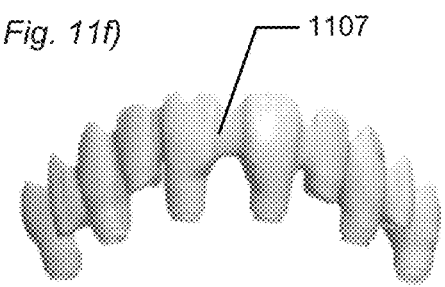
Figure 11G:
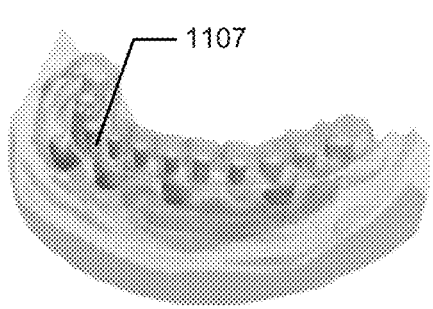

FIGS. 11b)-11g) show different examples of superstructures for joining a denture to a corresponding dental arch. The superstructure may be a bar, bridge etc, and the individual elements of the superstructure may be standard predetermined geometrical forms, such as tubes, cylinders, pipes, etc. or customized elements such as pins etc.

The superstructures in FIG. 11 are based on the positions and orientations of the dental implants (not visible) in the patient's dental arch. General and specific basic rules and requirements may be implemented in the software and thereby automate the provision of a superstructure. Thus, by means of the present invention a superstructure for a denture may be provided by automatic operation implemented in software.

FIG. 12 shows a schematic example of a process for virtually designing a denture.

Figure 12A:
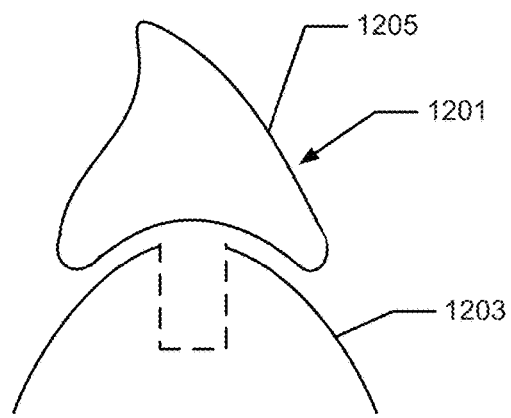
FIG. 12 shows a schematic example of a process for virtually designing a denture.

FIG. 12a) shows a schematic example of a part of a preliminary denture 1201, comprising an artificial tooth 1205, where the denture 1201 is arranged on a physical model of the patient's dental arch 1203.

First step in the process may be to scan the denture 1201 when the denture is arranged on the physical model of the patient's dental arch 1202.

The teeth side or occlusal or incisal surface of the denture is hereby acquired.

Figure 12B:
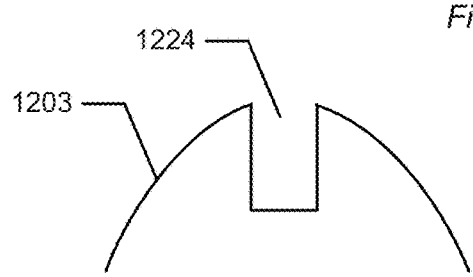

FIG. 12b) shows a schematic example of the physical model of the patient's dental arch 1202 without the denture arranged on it. A hole 1224 for an implant or implant analog can now be seen in the physical model of the patient's dental arch 1202. The hole could not be acquired in the first step because the denture blocked the view to the hole 1224.

Second step of the process may be to scan the physical model of the patient's dental arch 1202 with the implant hole 1224.

Scanning the physical model of the dental arch 1202 corresponds to scanning the gingival side, i.e. the underside, of the denture.

Figure 12C:
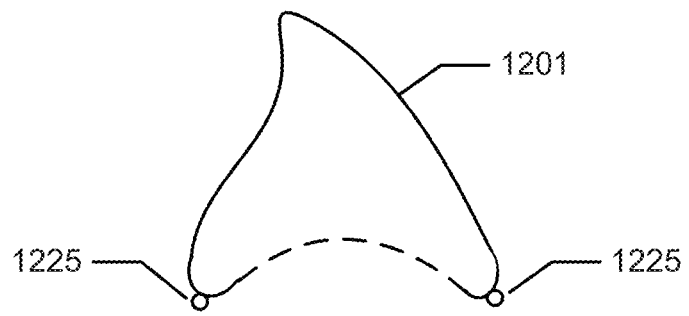
Figure 12C:
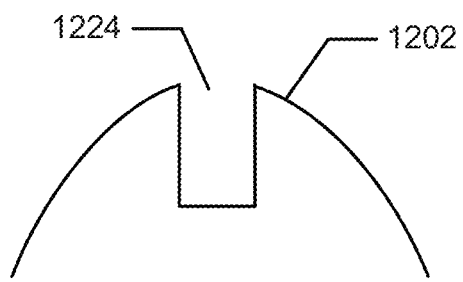
Figure 12C:
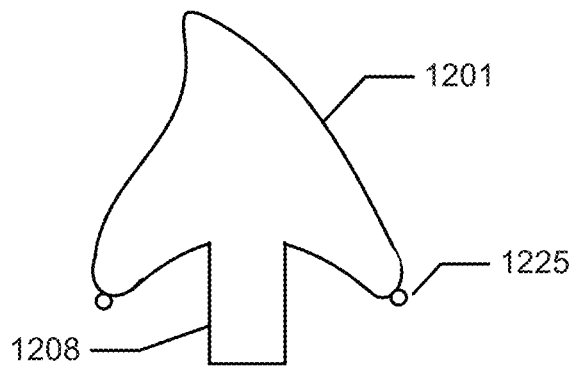

FIG. 12c) shows a schematic example of virtually combining the scan of the denture 1201 from FIG. 12a) with the scan of the dental arch 1202 comprising the implant hole 1224 from FIG. 12b).

A virtual spline 1225 may be virtually provided to the denture 1201 for designing the shape of the denture 1201.

When combining the scan of the denture 1201 with the scan of the dental arch 1202 all sides or surfaces of the denture may be acquired, and the result may be a 3D model of the denture 1201 which comprises both the teeth side or occlusal or incisal surface of the denture and the gingival side of the denture comprising the shape and/or position and/or orientation of the implant 1208.

Figure 12D:
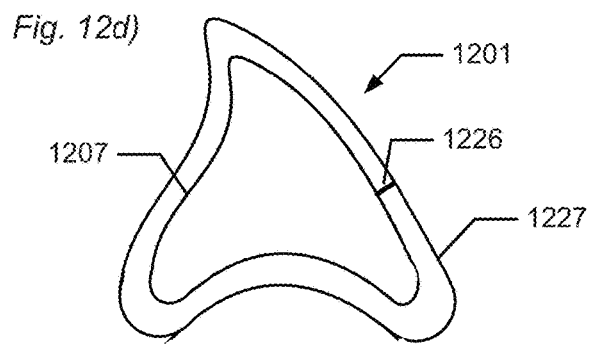

FIG. 12*d*) shows a schematic example of offsetting the shape of the denture 1201. The virtual model of the denture 1201 can be virtually modified by performing an offset or cutback 1226, marked with a line across, of the shape of the denture 1201. The size or thickness of the offset or cutback 1226 may correspond to the size or thickness of the planned veneering layer 1227 of the denture. The shape that is left after the offset or cutback 1226 has been performed may be the shape of the superstructure 1207.

Even though the schematic drawings in FIG. 12 and in the following FIGS. 13 and 14 are made in 2D, it is understood that the method is configured to be performed in 3D with 3D shapes of the denture etc.

Even though it is described in FIG. 12 that the physical model of the patient's dental arch is scanned, it is understood that the dental arch of the patient alternatively and/or additionally may be directly obtained from the dental arch of the patient, such as obtained by intra oral scanning.

Furthermore, the scanning of the denture may alternatively and/or additionally be performed directly in the mouth of the patient when the denture is arranged in the patient's mouth.

FIG. 13 shows schematic examples of how a denture can be scanned. The direction of the arrow in the figures indicates the direction from which the denture is scanned. The direction of the arrow in the figures indicates the direction from which the object is scanned. The object may be scanned in a hemisphere centered around the arrow.

The line 1328 in the figures indicates the plate in the scanner which the denture is arranged on when it is scanned.

Figure 13A:
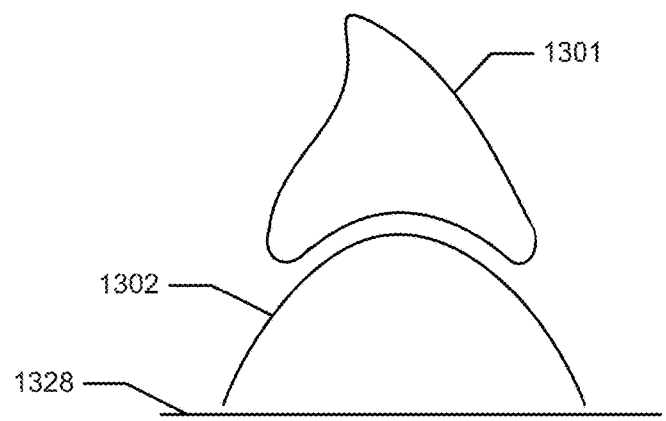
FIG. 13 shows schematic examples of how a denture can be scanned.

In FIG. 13*a*) the denture 1301 is scanned from the teeth side or occlusal or incisal surface when arranged on a physical model of the patient's dental arch 1202.

Figure 13B:
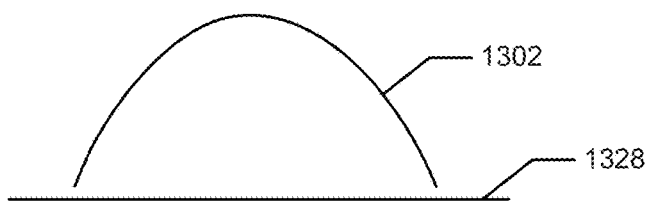

In FIG. 13*b*) the physical model of the patient's dental arch 1202 is scanned.

Scanning the patient's dental arch corresponds to scanning the gingival side of the denture.

By combining FIG. 13*a*) and FIG. 13*b*) all surfaces of the denture may be acquired.

Figure 13C:
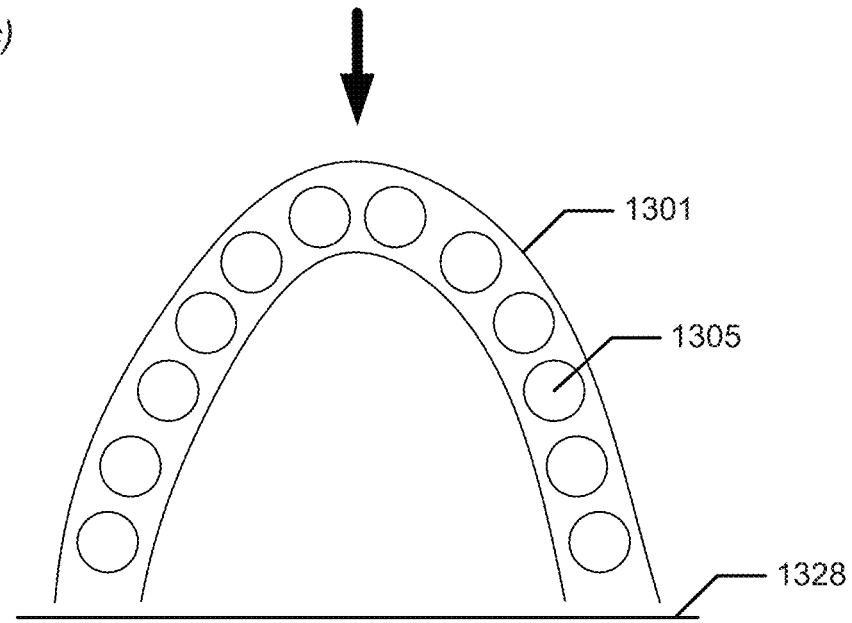

In FIG. 13*c*) the denture 1301 is scanned from the labial and buccal surface, i.e. the front surface or outside surface of the teeth in the denture.

Figure 13D:
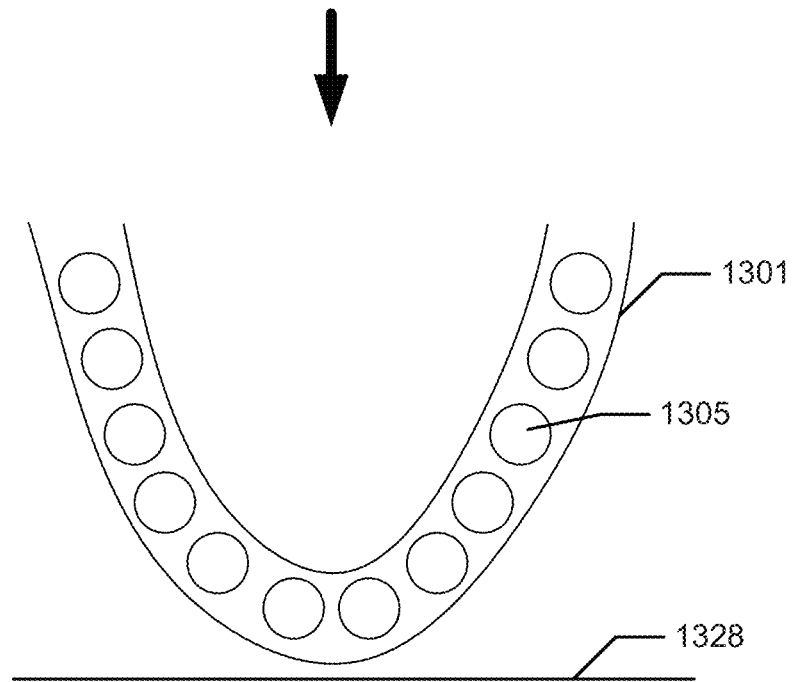

In FIG. 13*d*) the denture 1301 is scanned from the lingual surface, i.e. from the inside or tongue surface of the teeth in the denture.

By combining FIG. 13*c*) and FIG. 13*d*) all surfaces of the denture may be acquired.

Figure 13E:
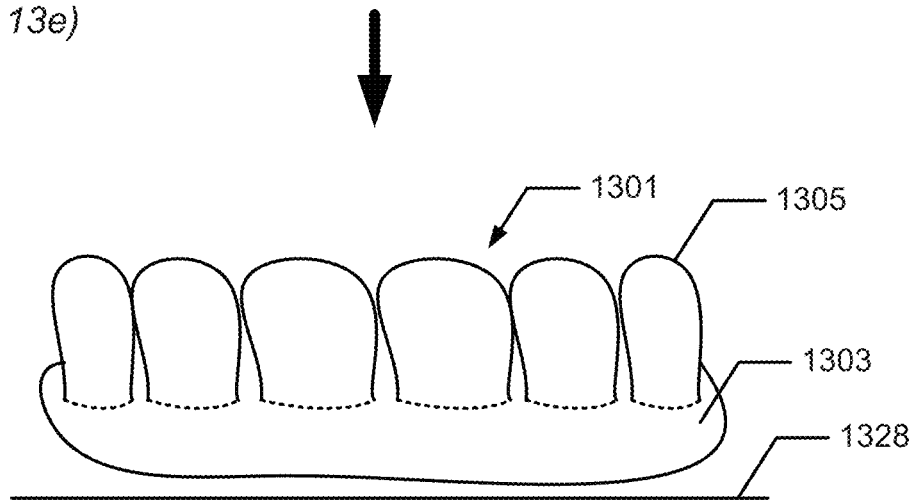

In FIG. 13*e*) the denture 1301 is scanned from the teeth side or incisal or occlusal surface.

Figure 13F:
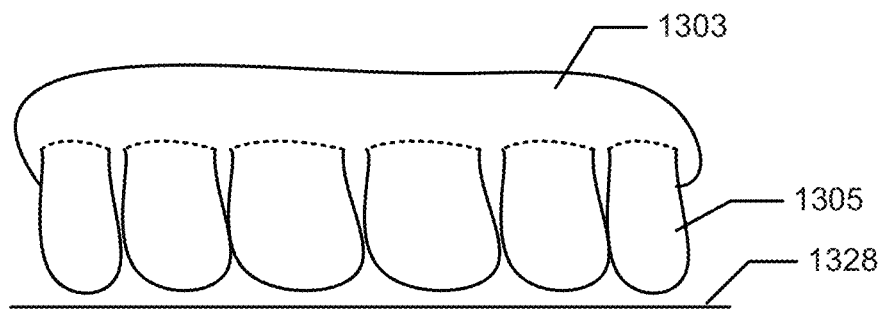

In FIG. 13*f*) the denture 1301 is scanned from the gingival surface.

By combining FIG. 13*e*) and FIG. 13*f*) all surfaces of the denture may be acquired.

Even though it is described in FIG. 13 that the physical model of the patient's dental arch is scanned, it is understood that the dental arch of the patient alternatively and/or additionally may be directly obtained from the dental arch of the patient, such as obtained by intra oral scanning. Furthermore, the scanning of the denture may alternatively and/or additionally be performed directly in the mouth of the patient when the denture is arranged in the patient's mouth.

FIG. 14 shows a schematic example of a process for virtually designing a denture.

The direction of the arrow in the figures indicates the direction from which the object is scanned. The object may be scanned in a hemisphere centered around the arrow.

The solid lines indicate which surfaces of the object, e.g. the denture, that will be captured in the scan. The broken or dotted lines indicate which surfaces of the object that will not be captured in this scan.

Figure 14A:
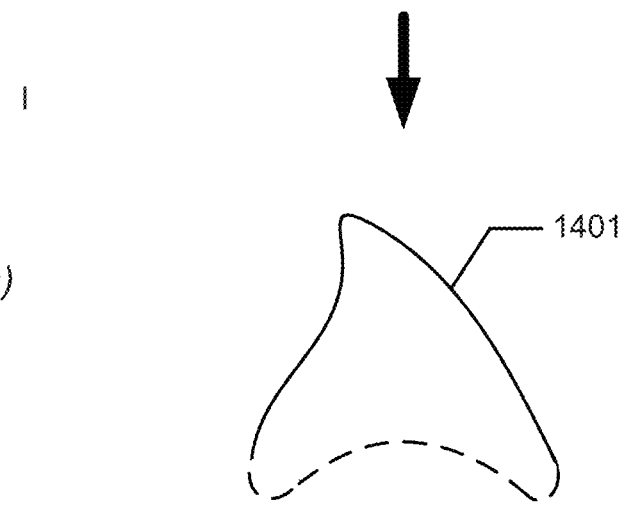
FIG. 14 shows a schematic example of a process for virtually designing a denture.

FIG. 14*a*) shows that the denture 1401 is scanned from above, i.e. from the teeth side or occlusal or incisal surface; denoted scan I.

Figure 14B:
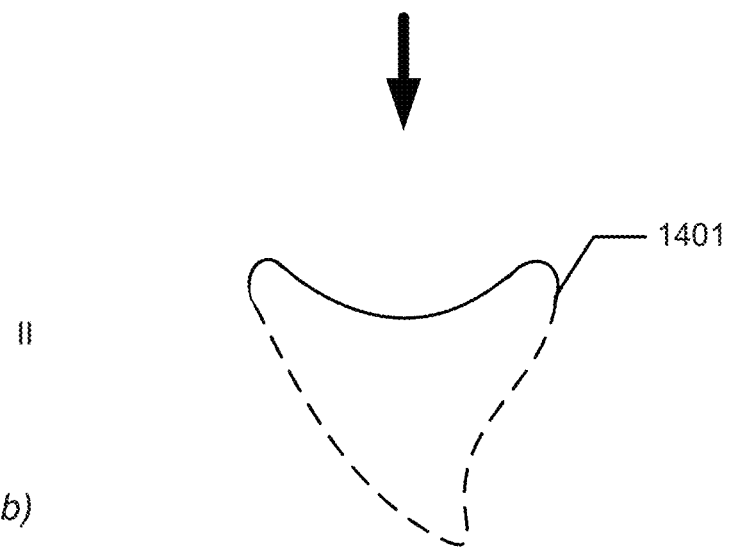

FIG. 14*b*) shows that the denture 1401 is scanned from below, i.e. from the gingival surface; denoted scan II.

In FIG. 14*c*) the scan I from FIG. 14*a*) and the scan II from FIG. 14*b*) are combined to give the resultant virtual model III of all surfaces of the denture 1401.

Figure 14D:
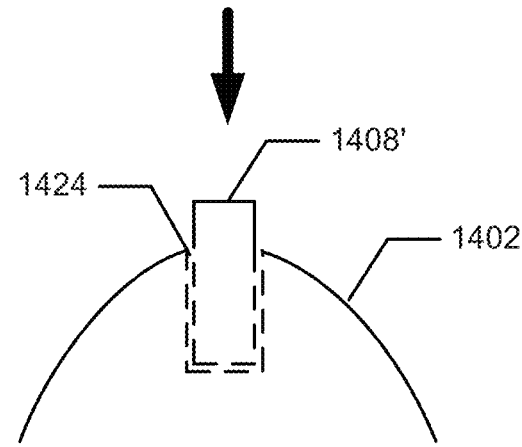

FIG. 14*d*) shows that the physical model of the patient's dental arch 1402 is scanned from above, when an implant analog 1408' is arranged in the hole 1424 for the implant, denoted scan IV.

Figure 14E:
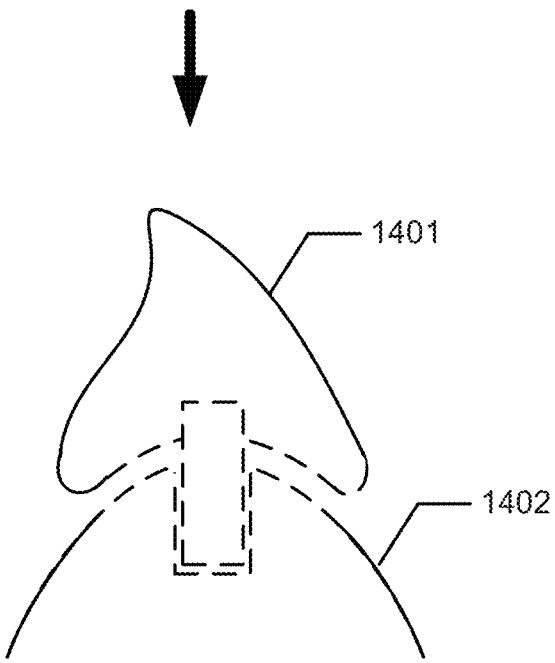

FIG. 14*e*) shows that the denture 1401 is scanned when arranged on the physical model of the patient's dental arch 1402; denoted scan V.

In FIG. 14*f*) the scan IV from FIG. 14*d*) and the scan V from FIG. 14*e*) are combined to give the resultant virtual model VI of the implant position and orientation in the dental arch of the patient.

In FIG. 14*g*) the virtual model III of the denture from FIG. 14*c*) and the virtual model VI of the implant positions and orientations from FIG. 14*f*) are aligned and combined to provide a model VII of the denture and the implant positions and orientations.

A virtual cutback or offset may be performed on the model VII to provide and determine the superstructure and a possible veneering layer, as shown in FIG. 12*d*).

Even though it is described in FIG. 14 that the physical model of the patient's dental arch is scanned, it is understood that the dental arch of the patient alternatively and/or additionally may be directly obtained from the dental arch of the patient, such as obtained by intra oral scanning. Furthermore, the scanning of the denture may alternatively and/or additionally be performed directly in the mouth of the patient when the denture is arranged in the patient's mouth.

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method for manufacturing a superstructure from a virtual model of the superstructure, the superstructure joining a denture and a corresponding dental arch, the method comprising:
    obtaining a first 3D representation of at least a part of a preliminary model of the denture,
    obtaining a second 3D representation of at least a part of the dental arch comprising dental implants,
    combining the first and second 3D representations to provide a third 3D representation of at least part of the preliminary model of the denture where the gingival side of the third 3D representation corresponds to the second 3D representation,
    generating a virtual model of the superstructure based on the third 3D representation, dental implant positions and dental implant orientations, and
    manufacturing the superstructure from the virtual model of the superstructure.

2. The method according to claim 1, wherein the generating a model of a superstructure is further based on template superstructure elements and/or predefined dental and superstructure parameters.

3. The method according to claim 1, wherein the method further comprises virtually modeling a superstructure based on the second 3D representation and/or the third 3D representation.

4. The method according to claim 1, wherein individual teeth and gingiva are segmented and each tooth is provided with an individual cut-back depending on its position in the dental arch.

5. The method according to claim 1, wherein at least a part of the preliminary model of the denture comprises a teeth side.

6. The method according to claim 1, wherein at least a part of the preliminary model of the denture comprises a gingival side.

7. The method according to claim 1, wherein providing at least part of the preliminary model of the denture comprises providing the entire preliminary model of the denture.

8. The method according to claim 1, wherein the first D representation is based on a physical preliminary model of the denture that is a wax-up of the preliminary denture or a try-in preliminary denture.

9. The method according to claim 1, wherein the second 3D representation is based on a physical model of the dental arch that is a gypsum model of the dental arch or the second 3D representation is directly obtained from the dental arch of the patient that is obtained by intra oral scanning.

10. The method according to claim 1, wherein the first and second 3D representations are acquired in the same coordinate system.

11. The method according to claim 1, wherein the preliminary model of the denture is 3D scanned while positioned on the dental arch or a physical model of the dental arch.

12. The method according to claim 1, wherein the third 3D representation is at least partly provided by subtracting the first 3D representation and the second 3D representation.

13. The method according to claim 1, wherein the superstructure is virtually modeled based on a template of a superstructure.

14. The method according to claim 1, wherein the predefined dental and superstructure parameters may be selected from the group of:
    minimum, maximum and preferred vertical distances between gingiva and superstructure,
    minimum, maximum and preferred vertical distances between superstructure and dental implants, and
    minimum, maximum and preferred cross sectional area of superstructure, and dental implants.

15. The method according to claim 1, further comprising segmenting teeth and gingiva and/or segmenting the individual teeth in first, second and/or third 3D representation.

16. The method according to claim 15, wherein the segmentation is at least partly based on texture information in the 3D representations.

17. The method according to claim 1, further comprising the step of subtracting an offset (cut-back) relative to the third 3D representation during the virtual modeling of the final denture.

18. The method according to claim 17, wherein the offset is a constant offset relative to the third 3D representation, relative to the occlusal side of the third 3D representation or relative to the gingival side of the third 3D representation.

19. The method according to claim 1, wherein a first offset is provided relative to the teeth in the third 3D representation and a second offset is provided relative to the gingiva in the third 3D representation.

20. The method according to claim 1, wherein a varying offset is provided relative to the third 3D representation, the value of said offset depending on the location on the third 3D representation.

21. The method according to claim 1, wherein individual teeth are provided with individual offsets depending on the location of the teeth.

22. The method according to claim 1, wherein an individual tooth is provided with a varying offset on the occlusal, gingival, facial and lingual sides.

23. The method according to claim 1, wherein the method further comprises:
    scanning the preliminary denture, where the denture is arranged on the dental arch, whereby the teeth side of the denture is obtained;
    scanning the dental arch without the preliminary denture, whereby the dental arch is obtained;
    combining the obtained scan of the teeth side of the denture with the obtained scan of the dental arch.

24. The method according to claim 1, wherein the method further comprises:
    scanning the dental arch, where an implant or implant analog is arranged in an implant bore in the dental arch, whereby the dental arch and the implant or implant analog are obtained;
    scanning the preliminary denture, where the denture is arranged on the dental arch with the implant or implant analog in the implant bore in the dental arch, whereby the teeth side of the denture is obtained;
    combining the obtained scan of the dental arch and the implant or implant analog with the obtained scan of the teeth side of the denture.

25. The method according to claim 1, wherein the method further comprises modeling pins on the dental implant bridge and corresponding holes in the denture to fit each other.

26. The method according to claim 25, wherein the holes in the denture are manufactured according to the corresponding pins in the bridge.

27. The method according to claim 1, wherein the method further comprises modeling dental implant pins and holes in the denture based on holes in pre-manufactured teeth.

28. A system for manufacturing a superstructure from a model of the superstructure, the superstructure joining a denture and a corresponding dental arch, the system comprising:
- a scanner for obtaining a first 3D representation of at least a part of a preliminary model of the denture,
- a scanner for obtaining a second 3D representation of at least a part of the dental arch comprising dental implants, and
- a computer configured to generate a model of a superstructure based on the first 3D representation, the second 3D representation, dental implant positions and dental implant orientations.

29. A method for manufacturing a superstructure from a model of the superstructure, the superstructure joining a denture and a corresponding dental arch, the method comprising:
- obtaining a first 3D representation of at least a part of a preliminary model of the denture, where the denture is arranged on the dental arch with an implant or implant analog in an implant bore in the dental arch, whereby a teeth side of the denture is obtained,
- obtaining a second 3D representation of at least a part of the dental arch comprising the implant or implant analog, where the implant or implant analog is arranged in the implant bore in the dental arch, whereby the dental arch and the implant or implant analog are obtained,
- combining the obtained 3D representation of the dental arch and the implant or implant analog with the obtained 3D representation of the teeth side of the denture,
- generating a model of a superstructure based on the first 3D representation, the second 3D representation, dental implant positions and dental implant orientations, and
- manufacturing the superstructure from the virtual model of the superstructure.

30. The method according to claim 1, wherein combining the first and second 3D representations provides a third 3D representation of an entirety of the preliminary model of the denture where the gingival side of the third 3D representation corresponds to the second 3D representation.

31. A method for manufacturing a superstructure from a virtual model of the superstructure, the superstructure joining a denture and a corresponding dental arch, the method comprising:
- obtaining a virtual model of the superstructure,
  - the virtual model of the superstructure being created by:
    - obtaining a first 3D representation of at least a part of a preliminary model of the denture,
    - obtaining a second 3D representation of at least a part of the dental arch comprising dental implants,
    - combining the first and second 3D representations to provide a third 3D representation of at least part of the preliminary model of the denture where the gingival side of the third 3D representation corresponds to the second 3D representation,
    - generating a virtual model of the superstructure based on the third 3D representation, dental implant positions and dental implant orientations, and
- manufacturing the superstructure from the virtual model of the superstructure.

* * * * *